Figure 1:
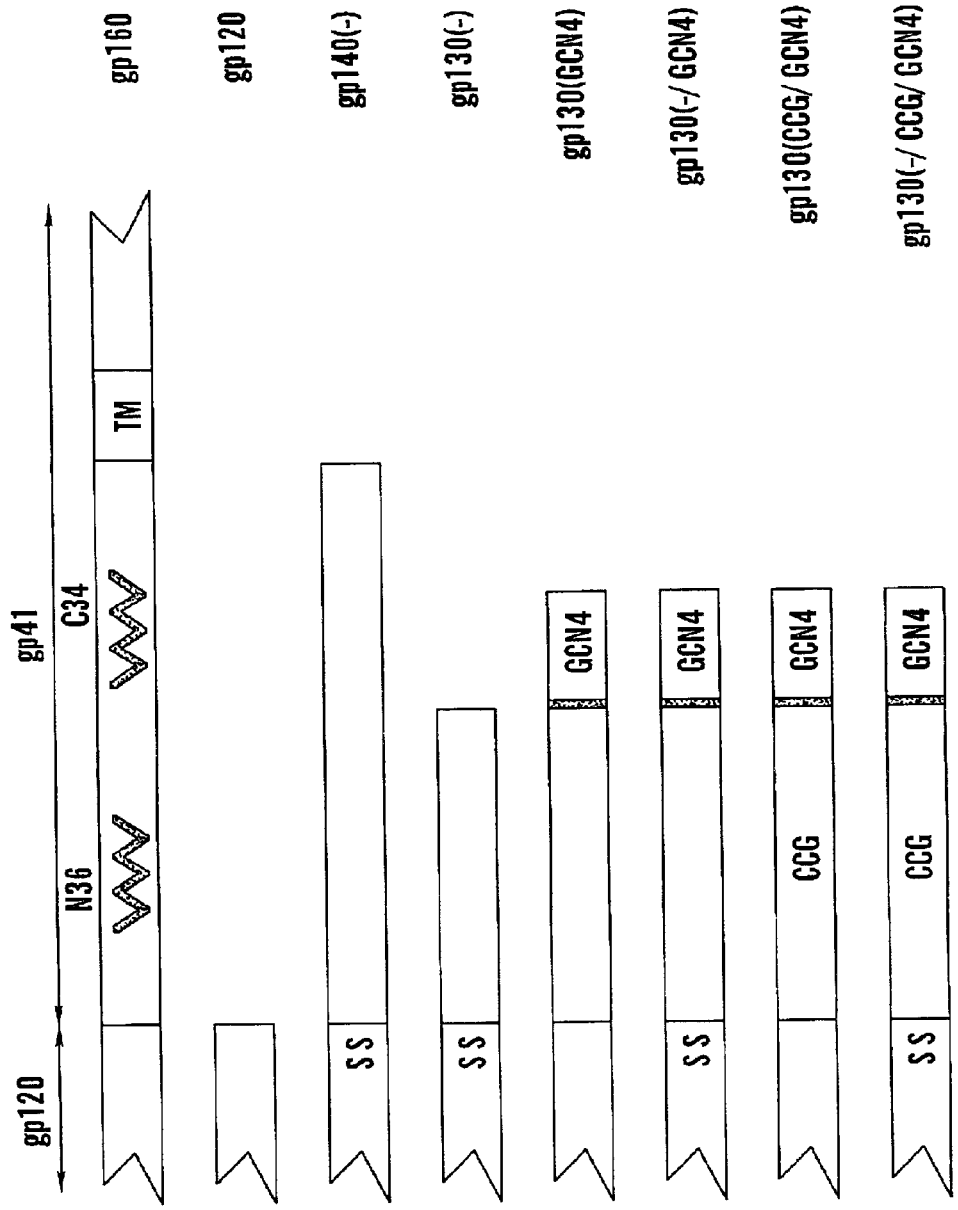

US006911205B2

(12) United States Patent
Sodroski et al.

(10) Patent No.: US 6,911,205 B2
(45) Date of Patent: Jun. 28, 2005

(54) STABILIZED SOLUBLE GLYCOPROTEIN TRIMERS

(75) Inventors: Joseph G. Sodroski, Medford, MA (US); Richard Wyatt, Andover, MA (US); Xinzhen Yang, Allston, MA (US); Michael Farzan, Brookline, MA (US); Peter D. Kwong, Washington, DC (US)

(73) Assignees: Dana-Farber Cancer Institute, Inc., Boston, MA (US); The Trustees of Columbia University, New York, NY (US)

( * ) Notice: Subject to any disclaimer, the term of this patent is extended or adjusted under 35 U.S.C. 154(b) by 27 days.

(21) Appl. No.: 10/100,534

(22) Filed: Mar. 18, 2002

(65) Prior Publication Data

US 2005/0106177 A1 May 19, 2005

Related U.S. Application Data

(63) Continuation of application No. PCT/US00/25557, filed on Sep. 18, 2000.

(60) Provisional application No. 60/154,677, filed on Sep. 17, 1999.

(51) Int. Cl.[7] ................................................ A61K 39/00

(52) U.S. Cl. ................................ 424/185.1; 424/186.1; 424/192.1; 424/208.1; 435/5; 530/300; 530/350; 536/23.4; 536/23.72

(58) Field of Search ........................... 424/185.1, 186.1, 424/192.1, 208.1; 435/5; 530/300, 350; 536/23.4, 23.72

(56) References Cited

U.S. PATENT DOCUMENTS 6,140,059 A 10/2000 Schawaller

FOREIGN PATENT DOCUMENTS

WO WO 99/16883 A2 4/1999

OTHER PUBLICATIONS

Burgess et al. Possible dissociation of the heparin–binding and mitogenic activities of heparin binding growth factor–1 from its receptor–binding activities by site directed mutagenesis of a single lysine residue. J. of Cell Bio..(199) vol 111, p 2129–2138.*

Lazar et al. Transforming growth factor alpha; mutations of aspartic acid 47 and leucine 48 results in different biological activities. Molecular and Cellular Biology (1988) vol. 8, No. 3, p 1247–1252.*

Tao et al. Studies of aglycosylated chimeric mouse–human IgG. The Journal of Immunology (1989) vol. 143 No. 8, p. 2595–2601.*

Farzan, M. et al., 72:7620–7625, (Sep., 1998).

Richmond et al., *J. of Virol.*, 72(11):9092–9100 (Nov. 1998).

Yang et al., *J. of Virol.*, 74(12):5716–5725 (Jun. 2000).

Yang et al., *J. of Virol.*, 75(3):1165–1171 (Feb. 2001).

Yang et al., *J. of Virol.*, 74(10):4746–4754 (May, 2000).

Binley et al., *J. of Virol.*, 74(2):627–643 (Jan., 2000).

Weissenhorn et al., *Nat'l Acad. of Science*, 94:6065–6069 (Jun., 1997).

Nautiyal et al., *Biochemistry*, 34(37):11645–11651 (Sep. 1995).

* cited by examiner

*Primary Examiner*—Ulrike Winkler
(74) *Attorney, Agent, or Firm*—Nixon & Peabody LLP

(57) ABSTRACT

The present application is directed to stabilized HIV envelope glycoprotein trimers. The trimers are stabilized by introducing trimeric motifs, preferably the GCN4 coiled coil or the fibritin trimeric domain at certain sites, for example in the gp41 ectodomain. These stabilized trimers or DNA molecules encoding such trimers can be used to generate an immunogenic reaction. The trimers can also be used in assays to screen for molecules that interact with them—and to identify molecules that interact with specific sites.

18 Claims, 14 Drawing Sheets

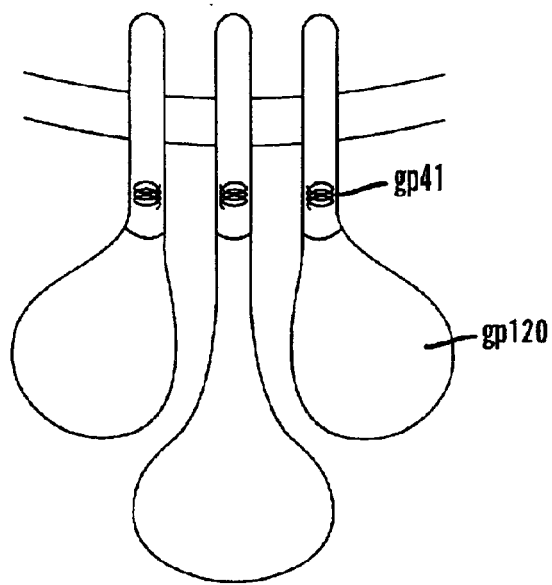
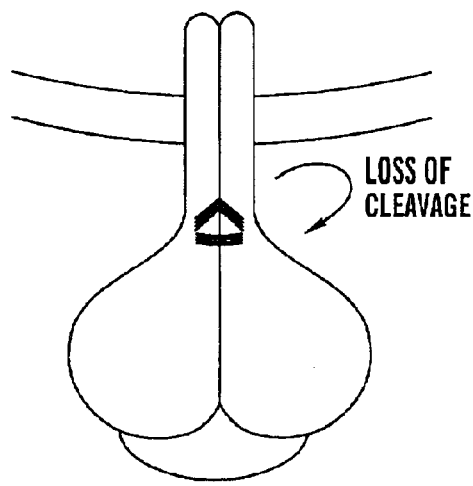
FIG. 6A
FIG. 6B
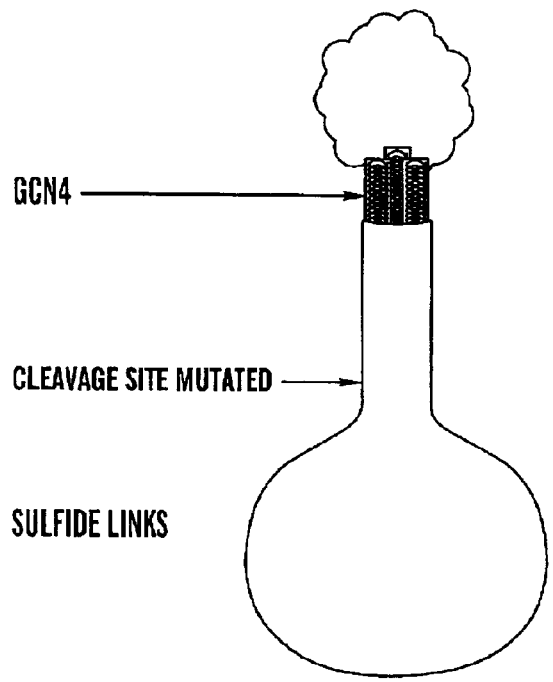
FIG. 6C

SEQUENCE LISTING

<160> NUMBER OF SEQ ID NOS: 4

<210> SEQ ID NO 1
<211> LENGTH: 32
<212> TYPE: PRT
<213> ORGANISM: Artificial Sequence -continued

```
<220> FEATURE:
<223> OTHER INFORMATION: Description of Artificial Sequence:  GCN4
      trimeric motif

<400> SEQUENCE: 1

Met Lys Gln Ile Glu Asp Lys Ile Glu Glu Ile Leu Ser Lys Ile Tyr
 1               5                  10                  15

His Ile Glu Asn Glu Ile Ala Arg Ile Lys Lys Leu Ile Gly Glu Val
            20                  25                  30

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: GP41 coiled
      coil motif

<400> SEQUENCE: 2

Tyr Leu Arg Asp Gln Gln Leu Leu
 1               5

<210> SEQ ID NO 3
<211> LENGTH: 48
<212> TYPE: PRT
<213> ORGANISM: Artificial Sequence
<220> FEATURE:
<223> OTHER INFORMATION: Description of Artificial Sequence: PK-C299
      Peptide

<400> SEQUENCE: 3

Tyr Thr His Ile Ile Tyr Ser Leu Ile Glu Gln Ser Gln Asn Gln Gln
 1               5                  10                  15

Glu Lys Asn Glu Gln Glu Leu Leu Ala Leu Asp Lys Trp Ala Ser Leu
            20                  25                  30

Trp Asn Trp Phe Gly Gly Gly Thr Glu Thr Ser Gln Val Ala Pro Ala
            35                  40                  45

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence:  Fibritin
      trimeric motif

<400> SEQUENCE: 4

Tyr Ile Pro Glu Ala Pro Arg Asp Gly Gln Ala Tyr Val Arg Lys Asp
 1               5                  10                  15

Gly Glu Trp Val Leu Leu Ser Thr Phe Leu
            20                  25
```

STABILIZED SOLUBLE GLYCOPROTEIN TRIMERS

This application is a continuation of copending application PCT/US00/25557, filed Sep. 18, 2000, incorporated herein by reference, which claims benefit of provisional applications 60/154,677, filed Sep. 17, 1999.

The present invention was supported in part by NIH grants AI24755, AI31783, AI39420, and Center for AIDS Research Grant AI28691 and the U.S. Government has certain rights thereto.

Human immunodeficiency virus type 1 (HIV-1) and type 2 (HIV-2) are the etiologic agents of acquired immunodeficiency syndrome (AIDS), which results from the profound depletion of CD4-positive lymphocytes in infected individuals (Barre-Sinoussi, F., et al., *Science* 220:868–71, 1983; Gallo, R. C., et al., *Science* 224: 500–3, 1984; Fauci, A. S., et al., *Ann Intern Med*. 100: 92–106, 1984).

Though great progress has been made in the treatment of individuals infected with HIV, numerous problems still remain. For example, treatment typically requires taking different medicines at different times over extended periods of time. The failure to do so can result in seriously undermining the treatment, and ultimately result in further progression of the disease. Even where individuals follow the treatment protocol, there are reports of disease progression. Moreover, the treatment is extremely costly, effectively rendering it out of reach to many individuals in the United States, and in much of the rest of the world.

Accordingly, the development of alternative methods of dealing with HIV infection is still extremely important.

One area where a great deal of attention has been extended has been in utilizing viral sub-units to generate immune reactions. Antibodies that neutralize viruses typically do so by inhibiting viral binding to surface receptors. The major protein found on the surface of HIV, and therefore a major target for generating neutralizing antibodies, is the envelope glycoprotein, gp120. This protein appears on the viral surface of the virion, thus rendering it a prime target for the immune system.

Unfortunately, the HIV-1 envelope glycoproteins have proven inefficient in generating antibodies that neutralize the virus, especially those that can neutralize more than a limited number of HIV-1 strains (Berman, P. W., et al., *J. Infect. Dis*. 176: 384–97, 1997; Connor, R. I., et al., *J. Virol*. 72: 1552–76, 1998; Mascola, J. R., et al., *J. Infect. Dis*. 173: 340–8, 1996; reviewed in Burton, D. R. and D. C. Montefiori, *AIDS* 11 *Suppl*. A: S87–98, 1997; Burton, D. R. and J. P. Moore, *Nature Med*. 4(5 Suppl.) 495–8, 1998; and Wyatt, R. and J. Sodroski, *Science* 280: 1884–8, 1998). Many of the antibodies elicited by the envelope glycoproteins are not able to bind efficiently to the functional envelope glycoprotein trimer and therefore are devoid of neutralizing activity (Broder, C. C., et al., *Proc. Natl. Acad. Sci. USA* 91: 11699–703, 1994; Moore, J. P., et al., *J. Virol*. 69: 101–9, 1995; Moore, J. P., et al., *J. Virol*. 70: 1863–72, 1996; Parren, P. W., et al., *Nature Med*. 3:366–7.1997; Parren, P. W., et al., *J. Virol*. 72: 3512–9, 1998; Wyat, R., et al., *J. Virol*. 71: 9722–31, 1997). The lability of the envelope glycoprotein trimers, conformational flexibility in the shed gp120 glycoprotein, and the variability and glycosylation of the gp120 surface all appear to contribute to the poor neutralizing antibody responses (reviewed in Montefiori, D. C., et al., *AIDS Res. Human Retroviruses* 15: 689–98, 1999; Moore, J., et al., *J. Virol*. 68: 469–84, 1995; and Wyatt, R., and J. Sodroski, *Science* 280: 1884–8, 1998).

The entry of primate lentiviruses such as HIV-1 and HIV-2 into target cells is mediated by the viral envelope glycoproteins (Wyatt, R., and J. Sodroski, *Science* 280: 1884–8, 1998). The mature envelope glycoproteins on the primate lentivirus are organized into an external gp120 (gp125 for HIV-2) exterior envelope glycoprotein and the gp41 transmembrane envelope glycoprotein (gp36 for HIV-2) (Alan, J. S., et al., *Science* 228: 1091–4, 1985; Earl, P. L., et al., *J. Virol*. 65: 2047–55, 1991; Robey, W. G., et al., *Science* 228: 593–595, 1985; Veronese, F. D., et al., *Science* 229: 1402–1405, 1985; Wyatt, R., and J. Sodroski, *Science* 280: 1884–8, 1998). For example, in the infected cell, the HIV-1 envelope glycoprotein is initially synthesized as an 845- to 870-amino acid protein, depending upon the viral strain (Earl, P. L., et al., *J. Virol*. 65: 2047–2055, 1991). N-linked, high-mannose sugars are added to this primary translation product to result in the gp160 envelope glycoprotein precursor (gp140 for HIV-2). Oligomers of gp160 form in the endoplasmic reticulum, and several pieces of evidence suggest that these are trimers. First, X-ray crystallographic studies of fragments of the gp41 ectodomain revealed the presence of very stable, six-helix bundles (Chan, D. C., et al., *Cell* 89: 263–73, 1997; Tan, K., et al., *Proc. Natl. Acad Sci. USA* 94: 12303–8, 1997; Weissenhorn, W., et al., *Nature* 387: 426–30, 1997). These structures were composed of a trimeric coiled coil involving N-terminal gp41 $\alpha$ helices, with three C-terminal gp41 $\alpha$ helices packed into the grooves formed by the three inner helices. Second, introduction of cysteine pairs at specific locations in the coiled coil resulted in the formation of intermolecular disulfide bonds between the gp160 subunits (Farzan, M., et al., *J. Virol*. 72: 7620–5, 1998). The disulfide-stabilized oligomer was shown to be a trimer. Finally, the matrix proteins of HIV-1 and the related simian immunodeficiency viruses, which interact with the intravirion domains of the envelope glycoproteins, crystallize as trimers (Hill, C. P., et al., *Proc. Natl. Acad. Sci. USA* 93: 3099–3104, 1996; Rao, Z., et al., *Nature* 378: 743–7, 1995).

Following oligomerization, the precursor glycoprotein is transported to the Golgi apparatus, where cleavage by a cellular protease generates external protein and the transmembrane-bound protein, e.g. the gp120 and gp41 glycoproteins (Alan, J. S., et al., *Science* 228: 1091–4, 1985; Robey, W. G., et al., *Science* 228: 593–595, 1985; Veronese, F. D., et al., *Science* 229: 1402–1405, 1985). The gp120 glycoprotein remains associated with the gp41 glycoprotein through non-covalent, hydrophobic interactions (Helseth, E., et al., *J. Virol*. 65:2119–23, 1991; Kowalski, M., et al., *Science* 237: 1351–1355, 1987). The lability of the gp120-gp41 association results in the "shedding" of some gp120 molecules from the trimer, resulting in non-functional envelope glycoproteins (McKeating, J. A., et al., *J. Virol*. 65: 852–60, 1991; Willey et al., *J. Virol*. 68: 1029–39, 1994). It has been suggested that these disassembled envelope glycoproteins result in the generation of high titers of non-neutralizing antibodies during natural HIV-1 infection (Burton, D. R., and J. P. Moore, *Nat. Med*. 4 (5 Suppl.): 495–8, 1998; Moore, J. P., and J. Sodroski, *J. Virol*. 70 1863–72, 1996; Parren, P. W., et al., *J. Virol*. 72: 3512–9). The envelope glycoprotein trimers that remain intact undergo modification of a subset of the carbohydrate moieties to complex forms before transport to the cell surface (Earl, P. L., et al., *J. Virol*. 65: 2047–55, 1991).

The mature envelope glycoprotein complex is incorporated from the cell surface into virions, where it mediates virus entry into the host cell. The gp120 exterior envelope glycoprotein binds the CD4 glycoprotein, which serves as a receptor for the virus (Dagleish, A. G., et al., *Nature* 312: 763–7, 1984; Klatzmann, D., et al., *Nature* 312: 767–8, 1984; McDougal, J. S., et al., *J. Immunol.* 137: 293–744, 1986). Binding to CD4 induces conformational changes in the envelope glycoproteins that allow gp120 to interact with one of the chemokine receptors, typically CCR5 or CXCR4 (Alkhatib, G., et al., *Science* 272: 1955–8, 1996; Choe, H., et al., *Cell* 85: 1135–48, 1996; Deng, H., et al., *Nature* 381: 661–6, 1996; Doranz, B. J., et al., *Cell* 85: 1149–58, 1996; Dragic, T., et al., *Nature* 381: 667–73, 1996; Feng, Y., et al., *Science* 272: 872–7, 1996; reviewed in Choe, H., et al., *Semin. Immunol.* 10: 249–57, 1998). The chemokine receptors are seven-transmembrane, G protein-coupled receptors, and gp120 interaction with the chemokine receptors is believed to bring the viral envelope glycoprotein complex nearer to the target cell membrane and to trigger additional conformational changes in the envelope glycoproteins. Although the exact nature of these changes is unknown, mutagenic data are consistent with a role for the hydrophobic gp41 amino terminus (the "fusion peptide") in mediating membrane fision (Cao, J., et al., *J. Virol.* 67: 2747–55, 1993; Freed, E. O., et al., *Proc. Natl. Acad. Sci. USA* 87: 46504, 1990; Helseth, E., et al., *J. Virol.* 64: 6314–8, 1990; Kowalski, M., et al., *Science* 237: 1351–5, 1987). It has been suggested that, following interaction of the "fusion peptide" with the target cell membrane, formation of the six-helical bundle by the three gp41 ectodomains would result in the spatial juxtaposition of the viral and target cell membranes (Chan, D. C., et al., *Cell* 89: 263–73, 1997). Six-helical bundles have been documented in several viral envelope glycoproteins that mediate membrane fusion and virus entry (Bullough, P. A., et al., *Nature* 371: 37–43, 1994; Carr, C. M., and P. S. Kim, *Cell* 73: 823–32, 1993; Weissenhorn, W., et al., *Proc. Natl. Acad. Sci. USA* 95: 6032–6, 1998; Weissenhorn, W., et al., *Mol. Cell* 2: 605–16, 1998). The formation of this energetically stable structure from a different and as-yet-unknown precursor structure is believed to provide the energy necessary to overcome the repulsion between the viral and cell membranes.

Initial attempts to generate immune reactions to HIV envelope glycoproteins have encountered substantial difficulties. For example, it was discovered that there are numerous regions in the glycoprotein which rapidly mutate in response to antibodies or drugs directed thereto. These regions also vary significantly from one strain of the HIV virus to another. Accordingly, these regions have been described as variable regions. There are other regions that are conserved among strains. Variable regions and conserved regions of gp120 have been mapped and are well known in the art. In the three-dimensional structure of the protein, these variable regions are typically at the surface, and thus mask the more conserved regions. The variable regions are highly antigenic, typically generating most of the antibodies seen. It is only late in the progression of the disease that antibodies generated to the conserved regions are typically seen. Such antibodies include the F105 antibody, the 17b antibody and the 48d antibodies. The amino acids comprising the epitopes for these antibodies are proximal to each other in the three-dimensional structure of the protein, but appear distant from each other when one looks strictly at a one-dimensional linear amino acid sequence. Such an epitope is referred to as a discontinuous conformational epitope. Furthermore, the amino acids comprising these discontinuous conformational epitopes are located in a number of conserved regions. Numerous variable-region deleted glycoproteins that expose these discontinuous conformational epitopes by deleting portions of the variable regions are disclosed in U.S. Pat. Nos. 5,817,316 and 5,858,366.

Consequently, it is clear that the three-dimensional structure of the protein is extremely important in terms of what the immune system actually sees. Unfortunately, the individual monomers do not typically form stable trimeric spikes that approximate the natural wild type confirmation. Thus, generating neutralizing antibodies depends upon stabilizing the three-dimensional, trimeric structure of the envelope glycoprotein.

Attempts have been made to stabilize trimers by stabilizing interactions in the gp41 segment, for example by introducing cysteine residues. However, this approach has not been entirely satisfactory when attempting to stabilize soluble glycoproteins. Yet, the ability to create soluble glycoproteins is extremely useful. For example, producing large quantities of these trimers in soluble forms, as opposed to membrane-bound subunits, substantially simplifies the isolation and purification process. Moreover, in vivo environments are further destabilizing for trimers. Thus, being able to stabilize the envelope glycoprotein molecule so that they remain in their trimeric state would be extremely useful. This is particularly so if one wants to use such trimers to elicit an immune response.

Different HIV isolates are able to infect different cells. All primary clinical HIV-1 isolates, defined as viruses that have not been passaged in immortalized cell lines, replicate in primary monocytes/macrophages and in primary T lymphocytes. Two groups of primary HIV-1 isolates have been defined, based on replication rate in peripheral blood mononuclear cells (PBMC) and the ability to infect and induce the formation of syncytia in immortalized CD4-positive cell lines (Asjo et al., 1986; Cheng-Mayer et al., 1988; Fenyo et al., 1988; Tersmette et al., 1988).

Most primary HIV-1 viruses that initiate human infection and that persist throughout the course of infection replicate to low levels in PBMC and do not replicate in immortalized T cell lines (Asjo et al., 1986; Schuitemaker et al., 1991; Schuitemaker et al., 1992; Connor et al., 1993, 1994 a,b). These viruses are referred to herein as macrophage-tropic primary isolates (sometimes referred to as "M"). In some HIV-1-infected individuals, viruses that replicate to higher levels in PBMC and that can infect and induce the formation of syncytia in immortalized CD4-positive cell lines emerge late in the course of infection (Asjo et al., 1986; Schuitemaker et al., 1992; Connor et al., 1993, 1994a,b). These viruses will be referred to herein as T cell line-tropic primary viruses (sometimes referred to as "T"). The T cell line-tropic primary viruses, by virtue of their ability to replicate in some immortalized cell lines, serve as precursors to the laboratory-adapted isolates, which have been extensively passaged on such cell lines. Laboratory adaptation, however, results in a loss of the ability of HIV-1 to replicate in primary monocyte/macrophage cultures (Schuitemaker et al., 1991; Chesebro et al., 1991; Westervelt et al., 1992; Valentin et al., 1994). Thus, while all HIV-1 isolates replicate on primary T lymphocytes, three groups of virus variants can be defined based on their ability to replicate in primary monocyte/macrophages or in immortalized T cell lines: (1) macrophage-tropic primary viruses that cannot infect T cell lines; (2) laboratory-adapted viruses that cannot infect primary monocytes/macrophages; and (3) T cell line-tropic primary viruses that exhibit dual-tropism for these cell types.

These changes limit the effectiveness of in vitro assays, particularly those that target the envelope proteins. Thus, the ability to create new in vitro assays to screen for molecules that can interact with the envelope glycoprotein is extremely important.

The G protein-coupled seven transmembrane segment receptor CXCR4, previously called HUMSTR, LCR-1 or LESTR (Federsppiel et al., 1993; Jazin et al., 1993; Loetscher et al., 1994) has been shown to allow a range of non-human, CD4-expressing cells to support infection and cell fusion mediated by laboratory-adapted HIV-1 envelope glycoproteins (Feng et al., 1996). Other G-protein-coupled seven transmembrane segment receptors such as CCR5, CCR3 and CCR2 have been shown to assist cellular entry of other HIV-1 isolates. It is believed that the cellular entry occurs as a result of the interaction of the external envelope glycoprotein, e.g., gp120, CD4 and the chemokine receptor.

These discoveries indicate the significant role the envelope glycoprotein plays in viral entry. They further illustrate its importance as a target for inhibiting the spread of infection, and the importance of having an in vitro screen for testing molecules that more closely approximates the wild type env to determine their effect on the external env.

SUMMARY OF THE INVENTION

We have now discovered that one can enhance the stability of the trimeric external envelope glycoprotein of a lentivirus, preferably a primate lentivirus, still more preferably a human immunodeficiency virus (HIV), e.g. the HIV-1 gp120 or HIV-2 gp125, by inserting additional coiled coils in a portion of the transmembrane glycoprotein, e.g. the HIV-1 gp41 or HIV-2 gp36, and removing the native cleavage site between, for example, the gp120 and gp41 portions in the gp160 precursor. For simplicity, we discuss the HIV-1 gp120, 41 and 160 glycoproteins below. We have found that it is advantageous, in the present invention however, not to form an anchored gp160 trimer, i.e. one that is membrane bound. Rather one removes the transmembrane region so that one has a soluble trimer. Although introduction of cysteine residues in the gp4 portion of the gp160 precursor resulted in a stable membrane anchored gp160 envelope glycoprotein, such substitutions were not sufficient for stabilizing the shortened soluble glycoproteins such as gp130 or gp140. By contrast, the introduction of a heterologous coiled coil at the carboxy portion in the soluble glycoproteins did have a major stabilizing influence.

In one preferred embodiment, the coiled coil can be from GCN4 by a C-terminal addition. GCN4 is a transcription factor that normally forms stable homodimers. However, introduction of hydrophobic residues at the a and d positions of the heptad repeats of the GCN4 dimerization motif increases the propensity of the protein to form trimers (Harbury et al., *Science* 262: 1401–7, 1993). One can extend the heptad repeat region and enhance the stability of the envelope glycoprotein by fusing the GCN4 trimeric motif (MKQIEDKIEEILSKIYHIENEIARIKKLIGEV) (SEQ ID NO: 1) C-terminal to the end of the gp41 coiled coil ( . . . YLRDQQLL) (SEQ ID NO: 2). In another preferred embodiment, the coiled coil can be from bacteriophage T4 fibritin by a C-terminal addition. Fibritin forms the whiskers and collar complex substructure embracing the T4 virion neck, and normally folds as a fibrous superhelical protein which consists of three identical polypeptide chains forming a parallel, segmented, alpha-helical structure. One can extend the heptad repeat region and enhance the stability of the envelope glycoprotein by fusing the fibritin trimeric (FT) sequence of 'YIPEAPRDGQAYVRKDGEWVLLSTFL' (SEQ ID NO: 4) C-terminal to the end of the gp41 coiled coil ( . . . YLRDQQLL) (SEQ ID NO: 2).

We have found we can form stable trimers containing the variable region-deleted monomer units (sometimes referred to as variable loop-deleted units) such as variable loop-deleted gp120 proteins (FIGS. 5 and 7). The stabilized trimers can also use combinations of different clades of the HIV-1 and 2 and using many different fragments from a transmembrane-deleted transmembrane protein. For example, a gp130 trimer, a gp140 trimer as well as gp160 transmembrane region-substituted trimers. In these examples, different lengths of the gp41 portion are used to produce the different proteins. For example, introducing a stop codon N-terminal to the natural precursor protein's transmembrane region. In one embodiment one can insert such a stop codon after Leu 593 in the primary R5HIV-1 isolate, YU2, resulting in a gp130 soluble glycoprotein. In another embodiment, one can insert a stop codon after Lys 683, which is located immediately N-terminal to the membrane-spanning region, resulting in a gp140 soluble glycoprotein. Thereafter a coiled coil such as GCN4 or fibritin is positioned at the carboxyl terminus, replacing the membrane-spanning region and cytoplasmic tail of the gp41 subunit. The proteolytic cleavage site is between the external glycoprotein and the transmembrane glycoprotein. It is preferably disrupted. For example, in HIV-1, the proteolytic cleavage site is between residues 508 and 511, based upon numbering using the prototypes HXBc2 strain. One can replace arginine residues 508 and 511 with serines. One can in addition insert a flexible linker (Gly) here to increasc conformational flexibility, thus allowing a closer mimicry of the cleaved, mature envelope glycoproteins. Other changes to prevent cleavage can also be accomplished by the skilled artisan based upon this disclosure.

These trimers can be used to elicit immune reactions. One typical method of eliciting such an immune reaction is what is known as "prime-boost" In this method, an envelope glycoprotein trimer is initially administered to a subject and at periodic times thereafter boosts are administered. The boosts can be an identical molecule or a somewhat different, but related, molecule. For example, one preferred strategy with the present invention would be to prime using a trimer formed of variable loop-deleted gp120 subunits and boosting periodically with trimers where the gp120 units are designed to come closer and closer to the wild type gp120 over the succession of boosts. For example, the first prime could be a variable loop-deleted gp120 where multiple variable regions were deleted, with a boost by the same trimer or a trimer where less amino acids from the variable loops were deleted, with subsequent boosts using trimers that had still less deletions or changes from the native gp120 conformation until the boosts were finally being given by trimers with a gp120 portion based on the native wild type HIV gp120.

One can also use cocktails containing a variety of different HIV strains to prime and boost with either a variety of different HIV strains or with trimers that are a mixture of multiple HIV strains. For example, the first prime could be with an envelope trimer from one primary HIV isolate, with subsequent boosts using trimers from different primary isolates. Similarly, the first prime could be with a trimer from a T-tropic virus, and subsequent boosts could be with trimers from M-tropic viruses.

The stabilized oligomer can be used to generate a range of antibodies that recognize and interact with a diverse range of HIV strains. The DNA sequence can also be used as a subunit vaccine.

In another embodiment, the stable trimers can be expressed in proteoliposomes, a stable expression system containing an integral membrane protein in a lipid membrane around an elliptoid or spherical shape. The shape contains an attractant such as streptavidin or avidin and the lipid membrane contains a moiety that binds to the attractant such as biotin. The integral membrane protein is bound to a ligand which is anchored in the shape. Methods for making proteoliposomes are provided in U.S. Ser. Nos. 60/173,675 and 60/207,596. In this embodiment, the stable trimers retain the transmembrane domain of gp41 to allow their incorporation into the proteoliposome.

In another embodiment, the stable trimers can be used in an in vitro assay. For example, one use is to identify molecules that will interact with the trimer. This can be done by known techniques such as tagging the trimers (e.g. with fluorescence, a chemical, biotin, etc.) to identify when a molecule binds to a trimer. Preferably, one can identify the sites where binding occurs. In this manner one can screen for molecules that for example block receptor binding.

One can also use these trimers in a prognostic assay. As discussed previously, it is only late in infection that broadly neutralizing antibodies are observed. These trimers can be used in an assay to screen readily for antibodies present in an infected individual's biological specimen. By monitoring the changes in the antibodies seen, one can make decisions and evaluations concerning the infected individual's health.

BRIEF DESCRIPTION OF THE DRAWINGS

FIG. 1 shows the structure of the soluble HIV-1 envelope glycoprotein variants. The partial structures of the soluble gp120, gp140 and gp130 envelope glycoproteins used are shown beneath the corresponding segment of the wild-type gp160 glycoprotein. The junction of gp120 and gp41, the positions of the N-terminal (N36) and C-terminal (C34) gp41 α helices, and the transmembrane (TM) region are shown. The DP178 peptide used in this study contains sequences corresponding to those of the C34 helix. The positions of the serine substitutions for arginine 508 and arginine 511 are shown (S S). The position of the Cys-Cys-Gly substitution in the N-terminal helical segment (residues 576–578) is shown (CCG). The position of the GCN4 trimeric peptide is also shown.

FIGS. 2A to 2C show the characterization of the soluble HIV-1 envelope glycoprotein variants. FIG. 2A shows sucrose density gradient fractions containing the soluble HIV-envelope glycoproteins. Fraction 1 was collected from the bottom of the gradient; fraction 11 (not shown) represents the top of the gradient. Fractions were precipitated by a mixture of sera from HIV-1-infected individuals. Precipitates were analyzed on SDS-polyacrylamide gels under non-reducing conditions, except for the samples (gp130(−/CCG/GCN4)+β-ME) shown in the bottom right panel, which were treated with 1.5% β-ME before gel analysis. Asterisks indicate the expected positions of a gp120 monomer in each gel. FIG. 2B shows radiolabeled envelope glycoproteins precipitated from transfected cell supematants by a mixture of sera from HIV-1-infected individuals and analyzed under non-reducing conditions (in the absence of β-ME). FIG. 2C shows precipitates of radiolabeled envelope glycoproteins were formed as in FIG. 2B and were analyzed on SDS-polyacrylamide gels after treatment with either 1.5% β-ME for 3 minutes at 100° C. or 5% β-ME for 10 minutes at 100° C.

FIG. 3 shows recognition of the soluble HIV-1 envelope glycoprotein variants by the DP178 gp41 peptide. Radiolabeled envelope glycoproteins in transfected cell supernatants were normalized for the amount of envelope protein and then precipitated either with a mixture of sera from HIV-1-infected patients (patient sera) or with a mixture of the 1D4 antibody and the PK-C299 peptide (DP178). The PK-C299 peptide contains the sequences of the DP178 peptide, which corresponds to the C-terminal gp41 helical region (see C34 in FIG. 1), and the sequences of the C9 peptide, which are recognized by the 1D4 antibody.

FIGS. 4A and B show recognition of the soluble HIV-1 envelope glycoprotein variants by monoclonal antibodies. Immunoprecipitation of the radiolabeled envelope glycoproteins was performed with a mixture of sera from HIV-1-infected individuals (patient sera) or with monoclonal antibodies. The precipitates were analyzed on SDS-polyacrylamide gels under reducing conditions. In FIG. 4A, the envelope glycoproteins were precipitated by a panel of anti-gp120 monoclonal antibodies that recognize discontinuous gp120 epitopes. The 39F antibody recognizes the gp120 V3 variable loop, the F91 antibody the gp120 CD4-binding site, and the 17b antibody a CD4-induced gp120 epitope. In FIG. 4B the envelope glycoproteins were precipitated by monoclonal antibodies against epitopes in the C1 C5 region of gp120: a discontinuous epitope involving the C1 and C5 regions (C11), and linear gp120 epitopes within the first (C1) conserved region (4D4#85 and 135/9) or within the fifth (C5) conserved region (670-30D and M91).

FIG. 5 is a drawing showing how the individual monomers form a stable soluble trimer.

FIG. 6 shows some additional constructs that form trimers. The legend is the same as in FIG. 1.

FIG. 7 shows that variable loop-deleted HIV-1 proteins are still trimeric. These proteins are based upon gp140 (see FIG. 1) where the V1 and V2 variable loops have been deleted (−V1/V2) and replaced with the sequence Gly-Gly-Gly. The GCN4 coiled coil is inserted at the carboxyl terminus. The resulting gp140 −V1/V2 is still trimeric as is the wild type gp140 (wt). Both are referred to as gp140T-−V1/V2 and gp140 T-wt, respectively. The monomer, is referred to as gp140M (over 2).

FIG. 8 shows the HIV-1 envelope glycoprotein immunogens used in Example 3. The linear map of the HIV-1 gp120 and gp41 envelope glycoproteins is shown in the top figure. The gp120 variable regions (V1–V5) and the gp41 alpha-helical regions (N36 and C34) and transmembrane region (TM) are indicated. The soluble gp120 envelope glycoprotein was produced by a plasmid in which a stop codon was introduced into the HIV-1 env gene (from either the YU2 or HXBc2 strain) such that the encoded protein was truncated immediately after arginine 508. In the gp130 and gp140 constructs, the gp120-gp41 cleavage site was altered by the introduction of serine substitutions for arginines at positions 508 and 511 (indicated by SS) (85, 86). The GCN4 trimeric motif (Harbury et al., *Science* 262: 1401–7, 1993) was added to the carboxyl terminus of some of the constructs (indicated by GCN4). The GCN4 motif was added immediately after the indicated gp41 amino acid residue, except in the gp140Δ683 (−/GCN4) construct, where two glycines separate the gp41 terminus and the GCN4 sequences.

FIG. 9 shows the structure of the soluble HIV-1 envelope glycoprotein variants. The top panel is a schematic diagram of the main sequence and structure properties of HIV-1 gp160. The five variable loops of gp120 and the N36 and C34 helices of gp41 are marked. The construct of gp140Δ683(−/GCN4) has a GCN4 trimeric motif fused after amino acid 683 of gp160. To express gp140Δ683(−/FT) glycoprotein, the fibritin trimeric (FT) sequence of 'YIPEAPRDGQAYVRKDGEWVLLSTFL' (SEQ ID NO: 4) was fused after amino acid 683 of gp160, just like in the gp140Δ683(−/GCN4) construct; and two glycine residues were inserted between the gp41 sequence and the fibritin sequence to allow some degree of structural flexibility of the final protein product. The cleavage site between gp120 and gp41 was also mutated to limit the protease cleavage.

FIG. 10 shows glycoproteins transiently expressed in 293T cells and labeled with $^{35}$S-methioninelcysteine. The $^{35}$S-labeled proteins were then immunoprecipitated with pooled sera of HIV-1-infected patients and resolved on a 7.5% SDS-PAGE gel. As previously shown, gp120 and gp140(−) were observed as monomeric on this type of gel and the gp140Δ683(−/GCN4) glycoprotein contained two forms, a reduced form of 140 kD and a high order form of about 400 kD which is consistent with a trimeric form. Shown in the right lane is the gp140Δ683(−/FT) glycoprotein which contained a similar high order form of around 400 kD and two reduced forms of 140 kD and 120 kD likely representing the un-cleaved and cleaved glycoproteins respectively.

FIGS. 11A–C show $^{35}$S-labeled proteins concentrated about 4-fold using Centriprep YM-30 filters (Amicon) and analyzed on 10% to 25% sucrose gradients. 1.1 ml fractions were taken manually, and protein distributions were analyzed by immunoprecipitating the proteins in each fraction with pooled sera of HIV-1-infected patients. Monomeric gp120 located in the fractions 6–7 as shown in FIG. 11B panel, while trimeric gp140 of gp140Δ683(−/GCN4) mainly concentrated in fractions 3–4 in 11C. The column bottom (fraction 1) probably contained some high order aggregates of the glycoprotein. In FIG. 11A, the majority of gp140Δ683 (−/FT) glycoprotein was in the fraction 3–4, which is consistent with a trimeric form, and the cleaved portion, as seen on the SDS-PAGE of FIG. 10, was in fractions 6–7, which is consistent with a monomeric form (Note: the column was shifted half of a fraction to the bottom due to an over-taking of fraction 1 up to about 1.7 ml).

FIGS. 12A and B show $^{35}$S-labeled gp120 mixed with a similar amount of $^{35}$S-labeled gp140Δ683(−/GCN4) or gp140Δ683(−/FT) proteins. FIG. 12A shows the results when the GCN4 trimeric motif was used, and FIG. 12B shows the results with the Fibritin trimeric motif. The proteins were allowed to compete to bind a panel of monoclonal antibodies in these mixtures. 3 μl of pooled patient sera or 1 μg of purified monoclonal antibodies were used in each competition assay in a standard immunoprecipitation format. The bound proteins were then resolved on a 7.5% SDS-PAGE gel (20×16 cm) and quantified by a PhosphorImager screen. The ratio of gp140 to gp120 for each antibody was calculated and normalized to that of the pooled patient sera. The bigger the gp140:gp120 ratio is, the higher the relative affinity of the gp140 trimer is to this specific monoclonal antibody. The profile of the gp140:gp120 ratio of a gp140 glycoprotein is reflective of the exposure or accessibility of the immunoepitopes on the trimeric complex. In this panel of monoclonal antibodies, B12 is highly neutralizing, F105 is modestly neutralizing, 17b and 48d are minimally neutralizing, and C11 and A32 are non-neutralizing. Thus, the exposure of epitopes on the gp140Δ683(−/FT) protein closely resembles that expected for the functional HIV-1 envelope glycoprotein complex.

DETAILED DESCRIPTION OF THE INVENTION

We have now discovered a stable soluble envelope glycoprotein trimer, and the DNA encoding the monomer units. Preferably the envelope glycoprotein is an envelope glycoprotein from a primate lentivirus. Still more preferably, it is from HIV-1 or HIV-2. Most preferably it is from HIV-1.

The primate lentiviruses share a general organizational similarity and the skilled artisan can readily determine the analogous structure in one virus from a review of the other. For example, both HIV-1 and HIV-2 have envelope glycoprotein precursors, gp160 and gp140, respectively, which are cleaved to an external protein, gp120 and gp125, respectively and a transdomain protein, gp41 and gp36, respectively. For ease of understanding, we will typically refer to the HIV-1 precursor and subunits, but the skilled artisan can readily use the same methodology with HIV-2. The trimer is stabilized by the insertion of coiled coils at the carboxy end. Preferably, the coiled coil is used to replace the transmembrane region when the coiled coil is inserted in the gp41 portion. The natural gp120/gp41 cleavage site is removed. For example, replacing arginine residues 508 and 511 with serines, using numbering based upon the prototypical HXBc2 strain. Other changes to prevent cleavage can readily be made by known techniques based upon the present disclosure. The transmembrane region of gp41 is also removed, so the trimer will be soluble. The resulting trimer forms spikes similar to that seen in the native wild type virus. Consequently, antibodies generated to these polypeptides are more likely to recognize and interact with native virus.

The importance of the envelope glycoprotein has been underscored by recent discoveries discussed above, such as the binding of gp120 to CD4 followed by interaction of the gp120-CD4 complex with one of the chemokine receptors, which are seven-transmembrane G protein-coupled receptors. The chemokine receptor interaction is believed to bring the viral envelope glycoprotein complex nearer to the target cell membrane and to trigger additional conformational changes in the envelope glycoproteins (Wu, L., et al., *Nature* 184:179–83, 1996; Trkola, A., et al., *Nature* 384:184–7, 1996). These changes are proposed to result in the interaction of the gp41 glycoprotein with the target host cell membrane, culminating in fusion of the host cell membrane with the viral membrane. Such a model is consistent with mutagenic analysis. Amino acid changes in the hydrophobic gp4 amino terminus (the "fusion peptide"), in the amino-terminal half of the ectodomain, or in the transmembrane region all result in fusion-defective envelope glycoproteins (Kowalski, M., et al., *Science* 237: 1351–5, 1987; Freed, E. O., et al., *Proc. Natl. Acad. Sci.* 87:4650–4, 1990; Cao, J., et al., *J. Virol.* 67: 2747–55, 1993). All these factors confirm the importance of the envelope glycoprotein.

Although an oligomeric form is seen in nature, being able to prepare a stable oligomer approximating the conformation of the oligomer formed naturally as discussed above has proven difficult. First, the HIV-1 envelope glycoprotein oligomer is naturally labile, disassociating into individual subunits readily. Secondly, molecules that are folded differently than the native HIV-1 envelope glycoproteins have limited usefulness in raising antibodies that recognize and neutralize the wild type viral envelope spike. Thus, our ability to stabilize these soluble envelope glycoproteins by using coiled coils other than the native coiled coils at or near the carboxyl terminus is surprising. This is particularly surprising since the transmembrane region possesses a coiled coil. Yet, merely preventing cleavage between the 2 proteins does not result in a soluble stable trimer.

One can use any coiled coil motif known to trimerize to stabilize the gp120 trimers. Coiled coil domains are comprised of heptad repeats with 2 characteristic hydrophobic amino acids found at the "a" and "d" residues of the helical wheel projection. Coiled coils may assemble into dimer, trimer, or tetramer bundles. The oligomeric form adopted by a particular coiled coil motif is largely a function of the amino acids found at the "a" and "d" positions, which form the inner core of the coiled coil bundle (Harbury et al., *Science* 262: 1401–1407, 1993; Wagschal et al.,*J. Mol. Biol.* 285: 785–803, 1999). gp41 contains coiled coil helices in its N terminus. In one preferred embodiment, the 32 amino acid trimeric motif of the leucine zipper protein GCN4 (MKQIEDKIEEILSKIYHIENEIARIKKLIGEV) (SEQ ID NO: 1) is fused C-terminal to the end ( . . . YLRDQQLL) (SEQ ID NO:2) of the gp41 coiled coil, thereby extending the heptad repeat region and increasing the potential stability of trimer association. In another preferred embodiment, the 26 amino acid trimeric motif of the bacteriophage T4 fibritin trimeric (FT) sequence, 'YIPEAPRDGQAYVRKDGEWV-LLSTFL' (SEQ ID NO: 4), is fused C-terminal to the end ( . . . YLRDQQLL) (SEQ ID NO:2) of the gp41 coiled coil, thereby extending the heptad repeat region and increasing the potential stability of trimer association.

Many trimeric motifs other than the GCN4 zipper domain and fibritin trimeric motif used here can be used in the gp41 portion to stabilize the gp120 trimer. Coiled coils other than GCN4 represent one such example. Preferably, one uses 4–5 heptad repeats of a given coiled coil domain, approximately 30 amino acids. Such motifs may be chosen either from coiled coil domains found in known proteins or from peptides designed de novo. For example, the fusogenic protein hemagglutinin of influenza virus is one of the first identified and best characterized trimeric coiled coil proteins (Wilson et al., *Nature* 289: 366–73, 1981), with a coiled coil domain of 27 amino acids. Another well studied example is heat shock transcription factor (Sorger and Nelson, *Cell* 59:807–13, 1989),which contains a coiled coil motif of 71 amino acids (Nomizu et al., *Int. J. Pept. Protein Res.* 40: 72–9, 1992). A large number of other proteins have been shown to contain trimeric coiled coil structures, including the 29 amino acid domain of vitamin-B12 receptor cubilin (Lindblom et al., *J. Biol. Chem.* 274: 6374–80, 1999), paramyxovirus fusion protein, with a 38 amino acid domain (Dutch et al., *Virology* 254: 147–159, 1999); vaccinia virus fusion protein, with a domain of 28 amino acids (*J. Virol.* 72: 7620–3, 1998); and macrophage scavenger receptor, with 22 heptad repeats, approximately 150 amino acids (Suzuki et al., *Biochemistry* 36: 15140–6, 1997). One can also use coiled coils from HIV-1 and HIV-2. However, these should not be in their native positions, unless one is inserting additional coiled coils in the protein. These examples represent only a portion of the list of proteins which contain trimeric and trimeric coiled coils.

One also can introduce de novo designed trimeric and trimeric coiled coil motifs into the gp41 protein. Advances in protein design have begun to make it possible to specifically design a protein or peptide which adopts a predicted conformation. Among the successes in the field of de novo protein design have been peptides containing coiled coil motifs, including trimeric bundling peptides (Harbury et al., *Science* 282: 1462–1467, 1998; Wagschal et al., *J. Mol. Biol.* 285: 785–803, 1999; Nautiyal et al., *Biochem.* 34:11645–51, 1999). Such peptides are typically around 30 amino acids and contain heptad repeats modeled on those found in known coiled coils, particularly with regard to the "a" and "d" amino acids, which direct assembly of the peptide helices into trimers (Harbury et al., *Science* 262: 1401–1407, 1993).

The trimeric motif, such as a coiled coil can be inserted at the junction between the gp120/gp41 proteins, or just within the gp41 region. Typically, the remainder of the gp41 region will not be used. Other sites could also be used for the introduction of the coiled coils (See FIG. 6). One can insert the coiled coil in place of the transmembrane region, and have the gp41 or gp36 protein terminate there or include the cytoplasmic domain. In some embodiments, one can insert multiple coiled coils.

In another embodiment one can also introduce cysteine residues at residues corresponding to the d and e positions of the coiled coil helix, preferably, of the native HIV coiled coil helix. For example, at positions corresponding to 576 and 577 of the HXBc2 isolate of HIV-1. These d and e residues are highly conserved among HIV-1 and HIV-2 strains and thus can readily be determined for all viruses. Other sites can also be used. These sites are numbered 555/556, 562/563, 569/570, and 583/584 in the HXBc2 HIV-1 sequence.

In order to maintain the overall conformation it is desirable to substitute an adjoining amino acid residue with one that provides flexibility in turning. Preferably, the residue is Gly. For example, substituting Gly for Ala at positions of the helix in the above example of 576/577 corresponds to position 578. Thus, LQA in the wild-type sequence is changed to CCG. Similarly, glycines could be introduced adjacent to the introduced cysteines, at positions 557, 564, 571 and 584, respectively. The equivalently positioned residues are easily identified in other HIV-1 and, in fact, in HIV-2 envelope glycoproteins as well based upon the general conservation.

These carboxyl inserted motifs such as coiled coil monomers are useful in producing stable trimers for structural or vaccine purposes, where the lability of these higher-order forms has been problematic. The insertion of the coiled coils, and optionally also the disulfide crosslinking of the HIV-1 and HIV-2 envelope glycoprotein trimers stabilizes otherwise labile neutralization epitopes specific for the trimer. The individual monomers can mask such natural epitopes by having biologically irrelevant epitopes that are exposed on the gp120 or gp160 monomer but actually buried on the functional trimer. Additionally, by stabilizing the trimeric structure, these changes can lengthen the half-life of the intact vaccine construct in the body.

Additionally, since these proteins have the transmembrane region deleted they will readily pass through the cell membrane of any producer cell. Therefore, they can readily be isolated from the cells without the need to isolate them from membrane fractions using severe detergents which further destabilize the trimers. Purification can be accomplished by known techniques.

The trimer complexes can be used to generate and also to identify a range of antibodies to gp120 and gp41. For example, antibodies that affect the interaction with the receptor binding sites can be directly screened for instance by using a direct binding assay. For example, one can use a radioactive or fluorescent marker to label gp120 protein or derivative and add-soluble CD4. There are various soluble CD4s known in the art including a two-domain (D1D2 sCD4) and a four-domain version. The labeled trimer, or derivative, e.g., a conformationally intact deletion mutant such as one lacking portions of the variable loops (e.g. V1/V2) and in some instances constant regions and soluble CD4 can be added to medium containing a cell line expressing a chemokine receptor that the antibody will block binding to. In this example, the derivative will block binding to CCR5. Alternatively, when using a derivative from a T cell tropic gp120 one would use a cell line that expresses CXCR4. Binding can then be directly measured. The antibody of interest can be added before or after the addition of the labeled trimer or derivative and the effect of the antibody on binding can be determined by comparing the degree of binding in that situation against a base line standard with that trimer or derivative, in the absence of the antibody.

A preferred assay uses the labeled trimer, or derivative portion, for example a trimer derived from an M-tropic strain such as JR-FL, iodinated using for instance solid phase lactoperoxidase (in one example having a specific activity of 20 $\mu$Ci/$\mu$g). The cell line containing the chemokine receptor in this example would be a CCR5 cell line, e.g. L1.2 or membranes thereof. Soluble CD4 could be present.

In one embodiment, the trimer is composed of variable region-deleted gp120 or gp125 such as described in U.S. Pat. Nos. 5,858,366 and 5,817,316. For example, the conformational gp120 portion should contain a sufficient number of amino acid residues to define the binding site of the gp120 to the chemokine receptor (e.g. typically from the V3 loop) and a sufficient number of amino acids to maintain the conformation of the peptide in a conformation that approximates that of wild-type gp120 bound to soluble CD4 with respect to the chemokine receptor binding site. In other embodiments the V3 loop can be removed to remove masking amino acid residues. In order to maintain the conformation of the polypeptide one can insert linker residues that permit potential turns in the polypeptides structure. For example, amino acid residues such as Gly, Pro and Ala. Gly is preferred. Preferably, the linker residue is as small as necessary to maintain the overall configuration. It should typically be smaller than the number of amino acids in the variable region being deleted. Preferably, the linker is 8 amino acid residues or less, more preferably 7 amino acid residues or less. Even more preferably, the linker sequence is 4 amino acid residues or less. In one preferred embodiment the linker sequence is one residue. Preferably, the linker residue is Gly.

In one preferred embodiment, the gp120 portion also contains a CD4 binding site (e.g. from the C3 region residues 368 and 370, and from the C4 region residues 427 and 457). The chemokine binding site is a discontinuous binding site that includes portions of the C2, C3, C4 and V3 regions. By deletion of non-essential portions of the gp120 polypeptide—such as deletions of portions of non-essential variable regions (e.g. V1/V2) or portions in the constant regions (e.g. C1, C5) one can increase exposure of the CD4 binding site. Another embodiment is directed to a gp120 portion containing a chemokine binding site. Similarly, by deleting the non-essential portions of the protein one can increase exposure of the chemokine binding site. The increased exposure enhances the ability to generate an antibody to the CD4 receptor or chemokine receptor, thereby inhibiting viral entry. Removal of these regions is done while requiring the derivative to retain an overall conformation approximating that of the wild-type protein with respect to the native gp120 binding region, e.g. the chemokine binding region when complexed to CD4. In addition, one can remove glycosylation sites that are disposable for proper folding. Maintaining conformation can be accomplished by using the above-described linker residues that permit potential turns in the structure of the gp120 derivative to maintain the overall three-dimensional structure. Preferred amino acid residues that can be used as linker include Gly and Pro. Other amino acids can also be used as part of the linker, e.g. Ala. Examples on how to prepare such peptides are described more fully in Wyatt, R., et al., *J. Virol.* 69: 5723–5733, 1995; Thali, M., et al., *J. Virol.* 67: 3978–3988, 1993; and U.S. Pat. Nos. 5,858,366 and 5,817,316, which are incorporated herein by reference.

An alternative gp120 derivative is one wherein the linkers used result in a conformation for the derivative so that the discontinuous binding site with the chemokine receptor approximates the conformation of the discontinuous binding site for the chemokine receptor in the wild-type gp120/CD4 complex. These derivatives can readily be made by the person of ordinary skill in the art based upon the above described methodologies and screened in the assays shown herein to ensure that proper binding is obtained.

In one embodiment, at least one sugar addition site is deleted. Preferably the sugar addition site is near a conformational epitope. This can be accomplished by known means. For example, the amino acid can be deleted. In one embodiment that deleted amino acid can be replaced by another residue that will not form a sugar addition site.

Figure 5A:
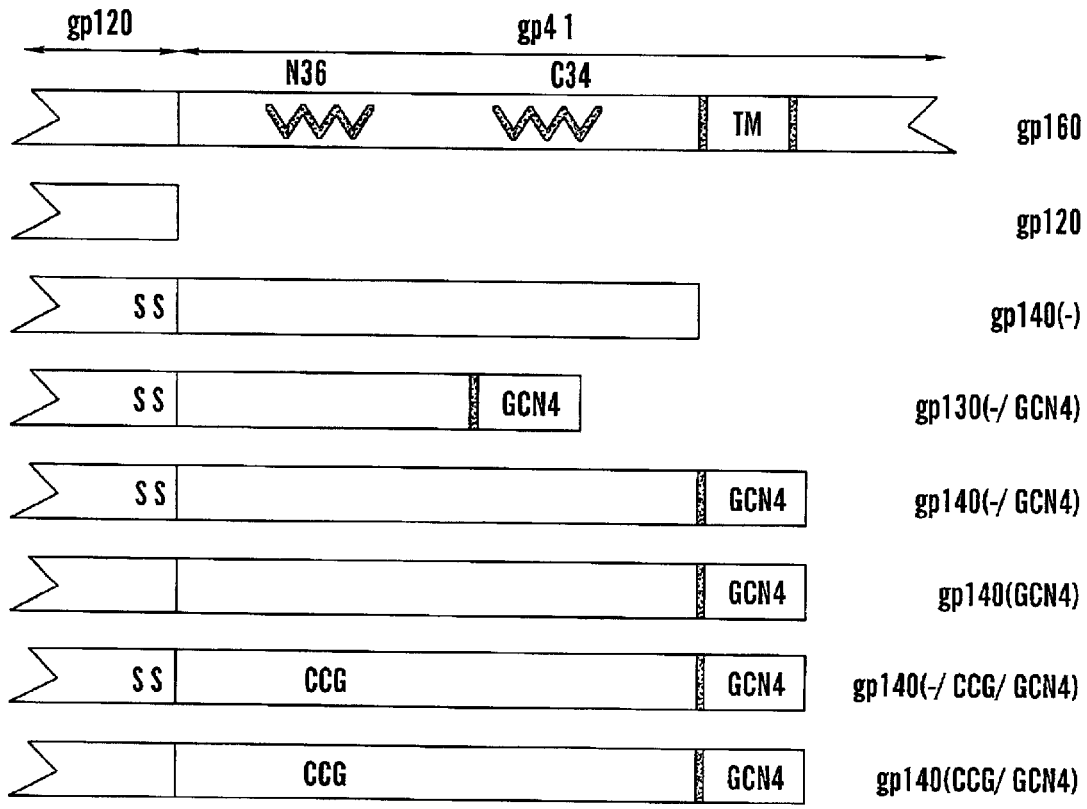
Figure 5B:
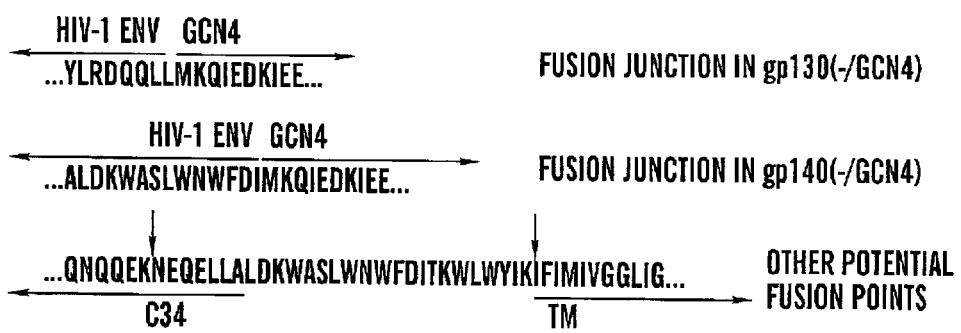
Figure 7:
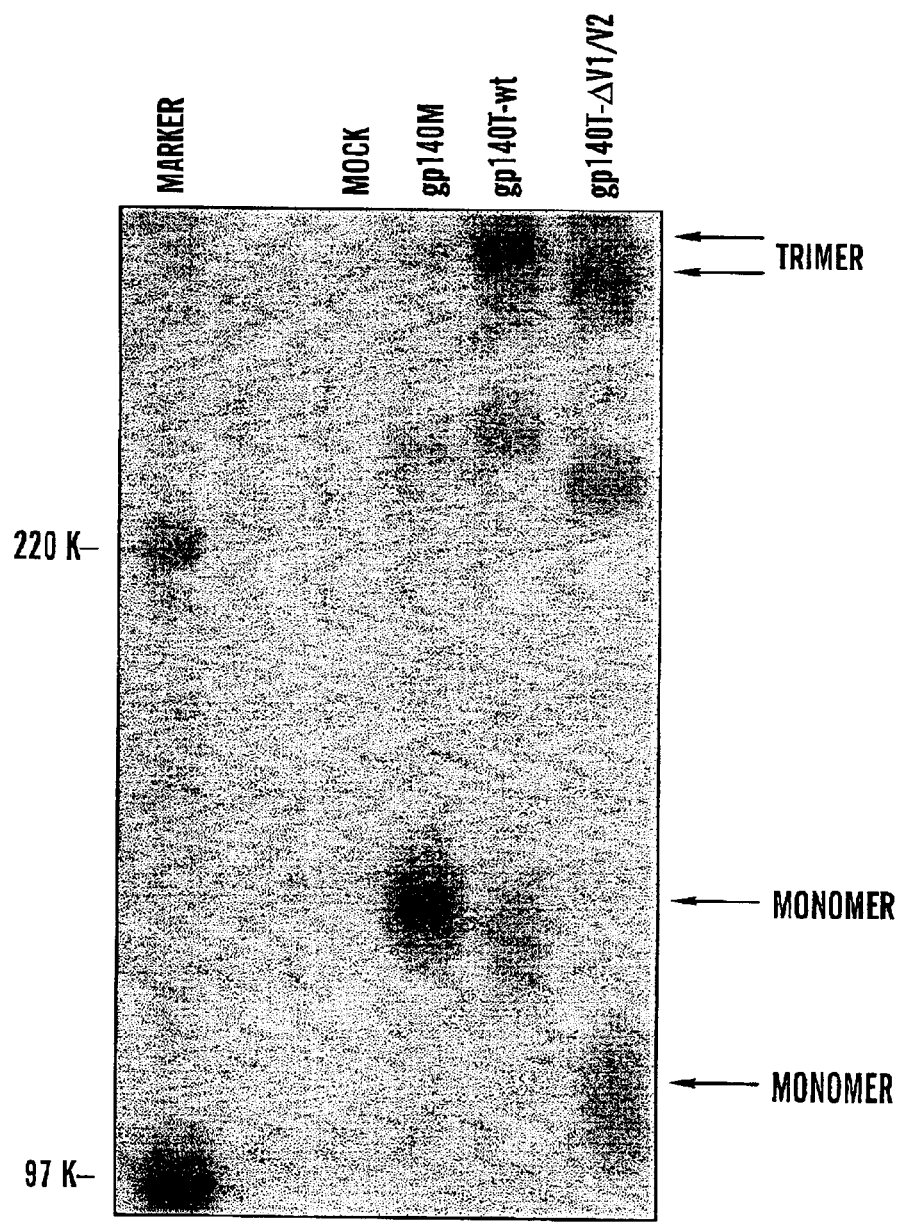
Figure 8:
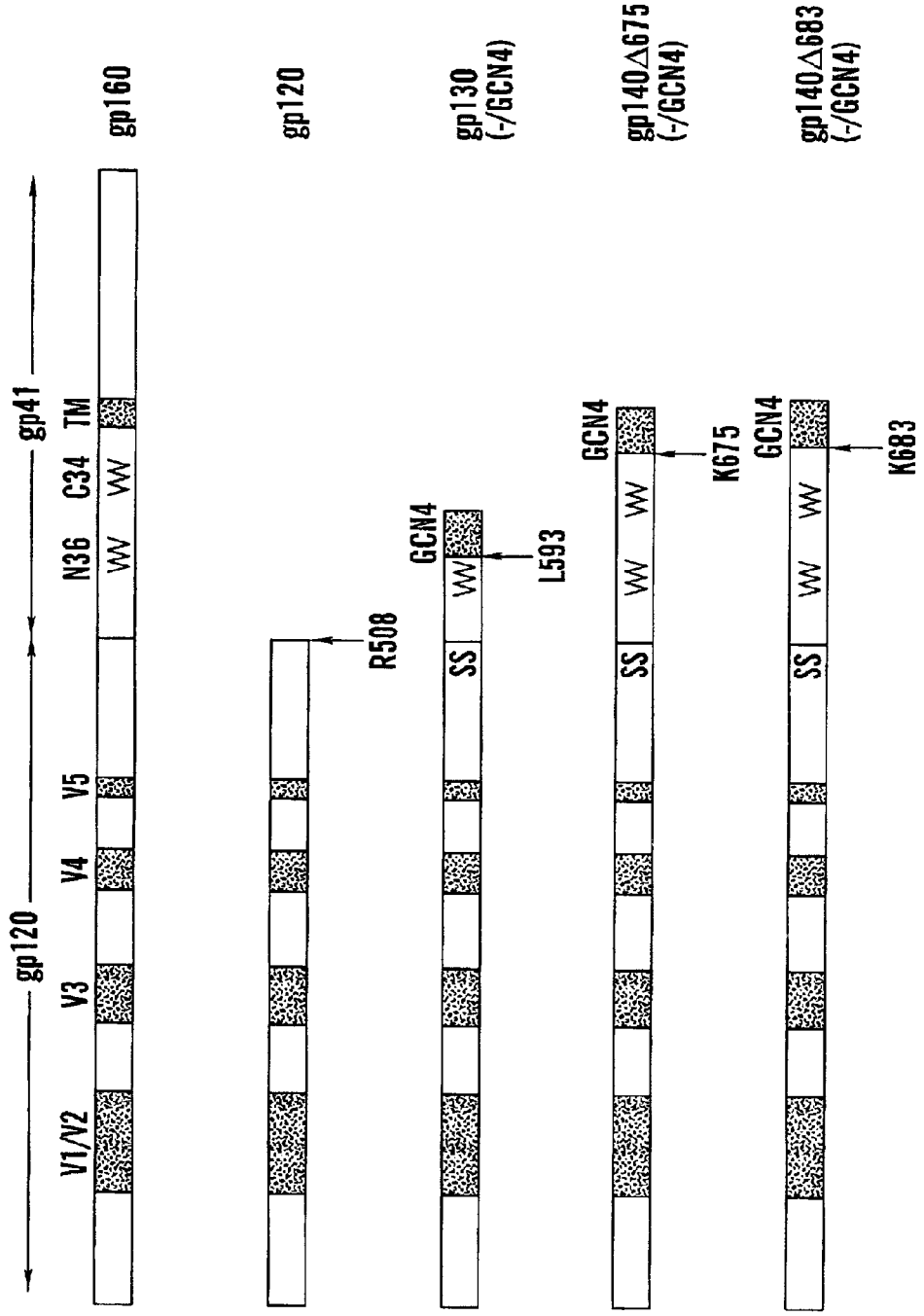

In a preferred embodiment, multiple sugar addition sites can be deleted. In a still more preferred embodiment the sugar addition sites can be deleted from the variable loop deleted monomers (FIGS. 5 and 7).

These proteins will lack the gp41 transmembrane region and will therefore be made as secreted, soluble proteins. For example, gp41 portions lacking the transmembrane region but retaining the cytoplasmic region, others truncated beginning with the transmembrane region, and therefore also lacking the cytoplasmic region. In an alternative embodiment, one can substitute amino acid residues in the transmembrane region with other amino acid residues that will not bind the membrane such as another coiled coil region. The desired changes can be accomplished by standard means using known techniques such as site directed mutagenesis. The resulting complex is a stable trimer having spikes similar to that found in the wild type. These immunogenic oligomers can be used to generate an immune reaction in a host by standard means. For example one can administer the trimeric protein in adjuvant. In another approach, a DNA sequence encoding the complex can be administered by standard techniques. The approach of administering the protein is presently preferred.

The protein is preferably administered with an adjuvant. Adjuvants are well known in the art and include aluminum hydroxide, Ribi adjuvant, etc. The administered protein is typically an isolated and purified protein. The protein is preferably purified to at least 95% purity, more preferably at least 98% purity, and still more preferably at least 99% purity. Methods of purification while retaining the conformation of the protein are known in the art. The purified protein is preferably present in a pharmaceutical composition with a pharmaceutically acceptable carrier or diluent present.

DNA sequences encoding these proteins can readily be made. For example, one can start with the native precursor of any of a range of HIV-1 or HIV-2 strains which are well known in the art and can be modified by known techniques, such as deleting the undesired regions, such as variable loops, and to insert desired coding sequences, such as the coiled coils, cysteines and linker segments. In addition to DNA sequences based upon existing strains, the codons for the various amino acid residues are known and one can readily prepare alternative coding sequences by standard techniques.

DNA sequences can be used in a range of animals to express the monomer, which then forms into the trimer and generates an immune reaction.

DNA sequences can be administered to a host animal by numerous methods including vectors such as viral vectors, naked DNA, adjuvant assisted DNA catheters, gene gun, liposomes, etc. In one preferred embodiment the DNA sequence is administered to a human host as either a prophylactic or therapeutic treatment to stimulate an immune response, most preferably as a prophylactic. One can administer cocktails containing multiple DNA sequences encoding a range of HIV envelope glycoproteins from different strains.

Vectors include chemical conjugates such as those described in WO 93/04701, which has targeting moiety (e.g. a ligand to a cellular surface receptor), and a nucleic acid binding moiety (e.g. polylysine), viral vector (e.g. a DNA or RNA viral vector), fusion proteins. such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include Moloney murine leukemia viruses and HIV-based viruses. One preferred HIV-based viral vector comprises at least two vectors wherein the gag and pol genes are from an HIV genome and the env gene is from another virus. DNA viral vectors are preferred. These vectors include herpes virus vectors such as a herpes simplex 1 virus (HSV) vector (Geller, A. I. et al., *J. Neurochem* 64: 487, 1995; Lim, F. et al., in *DNA Cloning: Mammalian Systems*, D. Glover, Ed., Oxford Univ. Press, Oxford England, 199); Geller, A. I., *Proc. Natl. Acad. Sci. USA* 90: 7603, 1993; Geller, A. I., *Proc. Natl. Acad. Sci. USA* 87: 1149, 1990), adenovirus vectors (LeGal LaSalle et al., *Science* 259: 988, 1993; Davidson, et al., *Nat. Genet* 3: 219, 1993; Yang, et al., *J. Virol.* 69: 2004, 1995), and adeno-associated virus vectors (Kaplitt, M. G., et al., *Nat. Genet.* 8:148, 1994). The DNA sequence would be operably linked to a promoter that would permit expression in the host cell. Such promoters are well known in the art and can readily be selected.

Stabilized forms of these complexes can readily be made, for example, by conjugates such as a poly(alkylene oxide) conjugate. The conjugate is preferably formed by covalently bonding the hydroxyl terminals of the poly(alkylene oxide) and a free amino group in the gp120 portion that will not affect the conformation of the discontinuous binding site. Other art recognized methods of conjugating these materials include amide or ester linkages. Covalent linkage as well as non-covalent conjugation such as lipophilic or hydrophilic interactions can be used.

The conjugate can be comprised of non-antigenic polymeric substances such as dextran, polyvinyl pyrrolidones, polysaccharides, starches, polyvinyl alcohols, polyacryl amides or other similar substantially non-immunogenic polymers. Polyethylene glycol(PEG) is preferred. Other poly(alkylenes oxides) include monomethoxy-polyethylene glycol polypropylene glycol, block copolymers of polyethylene glycol, and polypropylene glycol and the like. The polymers can also be distally capped with C1–4 alkyls instead of monomethoxy groups. The poly(alkylene oxides) used must be soluble in liquid at room temperature. Thus, they preferably have a molecular weight from about 200 to about 20,000 daltons, more preferably about 2,000 to about 10,000 and still more preferably about 5,000.

One can administer these stabilized compounds to individuals by a variety of means. For example, they can be included in vaginal foams or gels that are used as preventives to avoid infection and applied before people have sexual contact.

The peptides or antibodies when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 µg/kg a day, more preferably 1 to 10,000 µg/kg.

Routes of administration include oral, parenteral, rectal, intravaginal, topical, nasal, ophthalmic, direct injection, etc.

Changes in the viral envelope glycoproteins, in particular in the third variable (V3) region of the gp120 exterior envelope glycoprotein, determine tropism-related phenotypes (Cheng-Mayer et at., 1990; O'Brien et al., 1990; Hwang et al., Westervelt et al., 1992; Chesebro et al., 1992; Willey et al., *J. Virol.* 68: 1029–39, 1994). Amino acid changes in the V3 region (Helseth et al., *J. Virol.* 64: 2416–20, 1990; Freed et al., *Proc. Natl. Acad. Sci. USA* 87: 4650–4, 1991; Ivanoff et al., 1991; Bergeron et al., 1992; Grimaila et al., 1992; Page et al., 1992; Travis et al., 1992) and the binding of antibodies to this domain (Putney et al., 1986; Goudsmit et at., 1988; Linsley et al., 1988; Rusche et al., 1988; Skinner et al., Javeherian et al., 1989) have been shown to disrupt a virus entry process other than CD4 binding. Accordingly, one can create derivatives and change the phenotype for a particular receptor by substituting V3 loops.

One can inhibit infection by directly blocking receptor binding. This can be accomplished by a range of different approaches. For example, antibodies. One preferred approach is the use of antibodies to the binding site for these chemokine receptors. Antibodies to these receptors can be prepared by standard means using the stable immunogenic oligomers. For example, one can use single chain antibodies to target these binding sites.

As used herein the inhibition of HIV infection means that as compared to a control situation infection is reduced, inhibited or prevented. Infection is preferably at least 20% less, more preferably at least 40% less, even more preferably at least 50% less, still more preferably at least 75% less, even more preferably at least 80% less, and yet more preferably at least 90% less than the control.

One preferred use of the antibodies is to minimize the risk of HIV transmission. These antibodies can be included in ointments, foams, creams that can be used during sex. For example, they can be administered preferably prior to or just after sexual contact such as intercourse. One preferred composition would be a vaginal foam containing one of the antibodies. Another use would be in systemic administration to block HIV-1 or HIV-2 replication in the blood and tissues. The antibodies could also be administered in combination with other HIV treatments.

Pharmaceutical Compositions

An exemplary pharmaceutical composition is a therapeutically effective amount of an oligomer, antibody etc., that for example affects the ability of the receptor to facilitate HIV infection, or for the DNA sequence or the oligomer that can induce an immune reaction, thereby acting as a prophylactic immunogen, optionally included in a pharmaceutically-acceptable and compatible carrier. The term "pharmaceutically-acceptable and compatible carrier" as used herein, and described more fully below, includes (i) one or more compatible solid or liquid filler diluents or encapsulating substances that are suitable for administration to a human or other animal, and/or (ii) a system, such as a retroviral vector, capable of delivering the molecule to a target cell. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

In one preferred method of immunization one would prime with a trimer having variable loop deleted gp120, and then boost with a trimer that more closely approximates the wild type viral glycoprotein until at least one final boost with the stabilized wild type trimer. For example, if multiple variable regions and sugar addition sites are deleted from the priming trimer, the next boost will be with a trimer where more variable region amino acids are present and/or sugar addition sites present. Each boost will get closer to the wild type configuration until that configuration is reached.

One can also use cocktails containing a variety of different HIV strains to prime and boost with either a variety of different HIV strains or with trimers that are a mixture of multiple HIV strains. For example, the first prime could be with a mixture of envelope trimers from a number of primary HIV isolates, with subsequent boosts using trimers from these different primary isolates. Similarly, the first prime could be with a trimer from a M-tropic virus and also a T-tropic virus, and subsequent boosts could be with trimers from the T- and M-tropic viruses.

The stabilized oligomer can be used to generate a range of antibodies that recognize and interact with a diverse range of HIV strains. The DNA sequence can also be used as a subunit vaccine.

One can also prime and boost with one primary virus and then prime and boost with a second HIV virus such as another HIV primary virus envelope glycoprotein, and so on.

The stable trimers can be expressed in proteoliposomes, a stable expression system containing an integral membrane protein in a lipid membrane around an elliptoid or spherical shape. The shape contains an attractant such as streptavidin or avidin and the lipid membrane contains a moiety that binds to the attractant such as biotin. The integral membrane protein is bound to a ligand which is anchored in the shape. Methods for making proteoliposomes are provided in U.S. Ser. Nos. 60/173,675 and 60/207,596. In this embodiment, the stable trimers retain the transmembrane domain of gp41 to allow their incorporation into the proteoliposome. These stabilized proteoliposomes can be used in any number of ways such as immunogens or in assays.

The term "compatible", as used herein, means that the components of the pharmaceutical compositions are capable of being commingled with a small molecule, nucleic acid and/or polypeptides of the present invention, and with each other, in a manner such that does not substantially impair the desired pharmaceutical efficacy.

Doses of the pharmaceutical compositions of the invention will vary depending on the subject and upon the particular route of administration used. Dosages can range from 0.1 to 100,000 μg/kg per day, more preferably 1 to 10,000 μg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. In the embodiment where the prime is the variable loop deleted gp120 trimers, with the boost of native gp120, it is presently preferred to have a series of at least 2 boosts, preferably 3 to 5 boosts spread out over a year. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at 1442–43. (e.g., Hepatitis B Vaccine-type protocol); (ii) for example with other vaccines the recommended administration for children is first dose at elected date (at age 6 weeks old or older); a second dose at 4–8 weeks after first dose; a third dose at 4–8 weeks after second dose; a fourth dose at 6–12 months after third dose; a fifth dose at age 4–6 years old; and additional boosters every 10 years after last dose. See Product Information, *Physician's Desk Reference*, Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

One can as aforesaid also use cocktails where multiple HIV strains are present. In one embodiment one can use a trimer that is a mixture of multiple strains.

The antibodies, DNA sequences or oligomers of the invention may also be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof and are not excluded from the scope of this invention. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulfonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention also provides pharmaceutical compositions, for medical use, which comprise nucleic acid and/or polypeptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Other suitable routes of administration include intrathecal administration directly into spinal fluid (CSF), direct injection onto an arterial surface and intraparenchymal injection directly into targeted areas of an organ. Compositions suitable for parenteral administration are preferred. The term "parenteral" includes subcutaneous injections, intravenous, intramuscular, intrasternal injection or infusion techniques.

The compositions may conveniently be presented in unit dosage form and may be prepared by any of the methods well known in the art of pharmacy. Methods typically include the step of bringing the active ingredients of the invention into association with a carrier which constitutes one or more accessory ingredients.

Compositions of the present invention suitable for oral administration may be presented as discrete units such as capsules, cachets, tablets or lozenges, each containing a predetermined amount of the nucleic acid and/or polypeptide of the invention in liposomes or as a suspension in an aqueous liquor or non-aqueous liquid such as a syrup, an elixir, or an emulsion.

Preferred compositions suitable for parenteral administration conveniently comprise a sterile aqueous preparation of the molecule of the invention which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. F or this purpose any bland fixed oil may be employed including synthetic mono- or diglycerides. In addition, fatty acids such as oleic acid find use in the preparation of injectables.

Antibodies

The term "antibodies" is meant to include monoclonal antibodies, polyclonal antibodies and antibodies prepared by recombinant nucleic acid techniques that are selectively reactive with polypeptides encoded by nucleotide sequences of the present invention. The term "selectively reactive" refers to those antibodies that react with one or more antigenic determinants on e.g. gp120 and do not react with other polypeptides. Antigenic determinants usually consist of chemically active surface groupings of molecules such as amino acids or sugar side chains and have specific three dimensional structural characteristics as well as specific charge characteristics. Antibodies can be used for diagnostic applications or for research purposes, as well as to block binding interactions.

For example, a cDNA clone encoding a soluble stable gp120 trimer complex of the present invention may be expressed in a host using standard techniques (see above; see Sambrook et al., *Molecular Cloning; A Laboratory Manual*, Cold Spring Harbor Press, Cold Spring Harbor, N.Y.: 1989) such that 5–20% of the total proteins that can be recovered from the host is the desired protein. Recovered proteins can be electrophoresed using PAGE and the appropriate protein band can be cut out of the gel. The desired protein sample can then be eluted from the gel slice and prepared for immunization. Preferably, one would design a stable cell capable of expressing high levels of the protein(s) to be selected and used to generate antibodies For example, mice can be immunized twice intraperitoneally with approximately 50 micrograms of protein immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymed Corp., San Francisco, Calif. Mice whose sera contain detectable active antibodies according to the invention can be sacrificed three days later and their spleens removed for fusion and hybridoma production. Positive supernatants of such hybridomas can be identified using the assays described above and by, for example, Western blot analysis.

To further improve the likelihood of producing an antibody as provided by the invention, the amino acid sequence of polypeptides encoded by a nucleotide sequence of the present invention may be analyzed in order to identify desired portions of amino acid sequence which may be associated with receptor binding. For example, polypeptide sequences may be subjected to computer analysis to identify such sites.

For preparation of monoclonal antibodies directed toward polypeptides encoded by a nucleotide sequence of the invention, any technique that provides for the production of antibody molecules by continuous cell lines may be used. For example, the hybridoma technique originally developed by Kohler and Milstein (*Nature*, 256: 495–7, 1973), as well as the trioma technique, the human B-cell hybridoma technique (Kozbor et al., *Immunology Today* 4:72), and the EBV-hybridoma technique to produce human monoclonal antibodies, and the like, are within the scope of the present invention. See, generally Larrick et al., U.S. Pat. No. 5,001, 065 and references cited therein. Further, single-chain antibody (SCA) methods are also available to produce antibodies against polypeptides encoded by a eukaryotic nucleotide sequence of the invention (Ladner et al., U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or preferably to the stabilized trimers or to other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335–2549, 1984; Jansen, F. K., et al., *Imm. Rev.* 62:185–216, 1982; and Vitetta et al., supra).

Preferred linkers are described in the literature. See, for example, Ramakrishnan, S., et al., *Cancer Res.* 44: 201–208 (1984), describing the use of MBS (M-maleimidobenzoyl-N-hydroxysuccinimide ester). See also Umemoto et al., U.S.

Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6[3-(2-pyridyldithio)propionamido]hexanoate (Pierce Chem. Co., Cat #21651G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Complexes that form with molecules of the present invention can be detected by appropriate assays, such as the direct binding assay discussed earlier and by other conventional types of immunoassays. For example, a sandwich assay can be performed in which the receptor or fragment or other molecule of interest thereof is affixed to a solid phase. Incubation is maintained for a sufficient period of time to allow the trimer in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing for example, the trimer or antibody of interest bound to the immobilized molecule of the present invention is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The following Examples serve to illustrate the present invention, and are not intended to limit the invention in any manner.

EXAMPLE 1

Stabilization of Soluble Glycoprotein Trimers by the GCN4 Coiled Coil Motif

Materials and Methods

Envelope Glycoprotein Constructs. The envelope glycoprotein expression plasmids were derived from pSVIIIenv and were constructed by polymerase chain reaction or by QuikChange (Stratagene) site-directed mutagenesis. The specific changes introduced into each mutant are described in the Results, infra. The sequence of the entire env open reading frame was determined for each of the mutants. Two differences between the wild-type YU2 gp120 glycoprotein and the soluble gp120 glycoprotein were noted. One of these apparently arose as a result of PCR error and converted the wild-type alanine 379 to glutamine. In addition, a single glycine residue was introduced at the C-terminus of the gp120 glycoprotein, after the arginine at position 508. All of the other glycoproteins used in the study exhibited the wild-type sequence of the YU2 R5 viral envelope glycoproteins, except where modifications were deliberately introduced. Amino acid residue numbers are reported according to those of the prototypic HXBc2 sequences (Korber, B. B., et al., in *Human Retroviruses and AIDS*, Los Alamos National Laboratory, Low Alamos, N.Mex., 1998).

Envelope Glycoprotein Expression. To express the soluble HIV-1 envelope glycoproteins, a 100-mm dish of 293T cells was transfected with 4.5 µg of the pSVIIIenv plasmid expressing the mutant glycoproteins and 0.5 µg of an HIV-1 Tat-expressing plasmid. The transfection was performed using LipofectAMINE-PLUS™ reagent (Gibco-Lifetechnology) according to the manufacturer's recommendations. Sixteen hours after transfection, the cells were metabolically labeled with $^{35}$S-methionine/cysteine (NEN) in methionine/cysteine-free DMEM for 24 hours.

Sucrose Density Centrifugation. The oligomeric state of the envelope glycoprotein variants was investigated using sucrose density gradient centrifugation. The radiolabeled proteins in the transfected 293T cell supernatants were concentrated about three-fold (15-fold for the less efficiently secreted gp130(–) glycoprotein) using Centriprep 30 filters (Amicon). Approximately 750 µl of the concentrated supernatants were loaded onto 10 ml 10–25% continuous sucrose gradients, which were centrifuged in a Beckman SW41 rotor for 20 hours at 40,000 rpm at 4° C. Fractions of 1.1 ml were collected manually and precipitated using a mixture of sera from HIV-1-positive individuals and Protein A-Sepharose. Precipitates were analyzed on non-reducing and reducing SDS-polyacrylamide gels and autoradiographed. Molecular weights of the precipitated proteins were analyzed by interpolation, using previously characterized envelope glycoprotein dimers and trimers (Farzan, M., et al.,*J. Virol.* 72: 7620–5, 1998) and known molecular weight standards for reference.

Immunoprecipitation. Envelope glycoproteins were precipitated either by a mixture of sera from HIV-1-infected individuals or by a specific monoclonal antibody, as previously described (Wyatt, R., et al., *J. Virol.* 68:1029–39, 1994). Many of the antibodies studied were used in a previous study on antibody competition map of HIV-1 gp120, and referenced thereafter (Moore, J. P., et al.,*J. Virol.* 70: 1863–72, 1996).

Precipitation by the PK-C299 Peptide. The sequence of the PK-C299 peptide is as follows: YTHIIYSLIEQSQN-QQEKNEQELLALDKWASLWNWFGGGTETSQVAPA. (SEQ ID NO:3) The underlined N-terminus of this sequence corresponds to that of the DP178 peptide derived from the YU2 HIV-1 gp41 C-terminal coiled coil (Chen, C. H., et al., *J. Virol.* 69: 3771–7, 1995). The underlined C-terminus is derived from the C-terminus of bovine rhodopsin and can be recognized by the 1D4 antibody (Oprian, D. D,. et al., *Proc. Natl. Acad. Sci.* 84: 8874–8878, 1987). The sequence 'GGG' was included in the peptide to introduce potential structural flexibility between the DP178 helix and the bovine rhodopsin peptide tag. PK-C299 was custom synthesized by the Protein Chemistry Core Facility at the Howard Hughes Medical Institute, Columbia University. Metabolically labeled ($^{35}$S-Met/Cys) gp130(−) and gp130(−/GCN4) glycoproteins were incubated with a 20-fold molar excess of PK-C299 for 1 hour at 37° C. The glycoprotein/peptide complex was then precipitated by 5 μg of the 1D4 antibody.
Results The functional unit of the human immunodeficiency virus (HIV-1) envelope glycoproteins is a trimer composed of three gp120 exterior glycoproteins and three gp41 transmembrane glycoproteins. The lability of intersubunit interactions has hindered the production and characterization of soluble, homogeneous envelope glycoprotein trimers. Modifications that stabilize soluble forms of HIV-1 envelope glycoprotein trimers include disruption of the proteolytic cleavage site between gp120 and gp41, introduction of cysteines that form intersubunit disulfide bonds, and addition of a coiled coil such as GCN4 trimeric helices (FIG. 5): Characterization of these secreted glycoproteins by immunologic and biophysical methods indicates that these stable trimers retain structural integrity. The efficacy of the GCN4 sequences in stabilizing the trimers, the formation of intersubunit disulfide bonds between appropriately placed cysteines, and the ability of the trimers to interact with a helical, C-terminal gp41 peptide (DP178) indicate the N-terminal gp41 coiled coil exists in the envelope glycoprotein precursor and contributes to intersubunit interactions within the trimer.
Production and Characterization of Soluble HIV-1 Envelope Glycoproteins.

A variety of soluble forms of the HIV-1 envelope glycoprotein trimers are shown in FIG. 1. The first has a disruption of the proteolytic cleavage site between the gp120 and gp41 subunits by replacing arginine residues 508 and 511 with serines. The second has the introduction of a cystieine pair (and an adjacent glycine) into residues 576–578, which are located in the N-terminal (N36) gp41 helix. The introduced cysteines occupy the d and e positions of the heptad repeat, and thus are located within the hydrophobic interior of the gp41 α-helical coiled coil. Identical cysteine substitutions result in the covalent cross-linking of the full-length HIV-1 gp160 envelope glycoprotein subunits (Farzan, M., et al., *J. Virol.* 72: 7620–5, 1998). The third has an extension of the N-terminal gp41 coiled coil by the C-terminal addition of GCN4 sequences. GCN4 is a transcription factor that normally forms stable homodimers. However, introduction of hydrophobic residues at the a and d positions of the heptad repeats of the GCN4 dimerization motif increases the propensity of the protein to form trimers (Harbury, P. B., et al., *Science* 262: 1401–7, 1993). We fused the GCN4 trimeric motif (MKQIEDKIEEILSKIYHIENEIARIKKLIGEV) (SEQ ID NO: 1) C-terminal to the end ( . . . YLRDQQLL) (SEQ ID NO:2) of the gp41 coiled coil, thereby extending the heptad repeat region and the potential stability of trimer association.

All of the envelope glycoproteins used in this study (FIG. 1) were derived from the primary R5 HIV-1 isolate, YU2. Stop codons were introduced into the env gene (Genebank access number is M93258), resulting in termination of the proteins N-terminal to the natural gp160 membrane-spanning (TM) region. Thus, the majority of the envelope glycoproteins were secreted into the medium of expressing cells. To express soluble gp120, the YU2 envelope glycoprotein was terminated after arginine 508. Soluble gp130 glycoproteins contained all of the YU2 envelope glycoprotein residues up to and including leucine 593, which is located near the C-terminus of the gp41 coiled coil. The soluble gp140 glycoprotein was terminated after leucine 669, which is located immediately N-terminal to the membrane-spanning region. The presence of modifications designed to increase trimer stability in the mutants is indicated in parentheses in the mutant name. Thus, a (−) sign indicates the 508/511 RR/SS changes affecting gp120-gp41 proteolytic processing; "CCG" indicates the substitution of the cysteine pair and a glycine residue at positions 568–578; and "GCN4" indicates the presence of the GCN4 trimeric peptide at the carboxyl terminus of the protein.

Our initial studies indicated that, in contrast to the results seen for the membrane-anchored gp160 envelope glycoprotein, the CCG substitutions were not sufficient to cross-link the subunits of either soluble gp130 or gp140 glycoproteins (data not shown). Therefore, in this report we focus on the effects of the cleavage site modification and CCG substitution in the context of soluble glycoproteins containing the GCN4 trimeric motif, which was found to have a major stabilizing influence (see below).

Figure 2A:
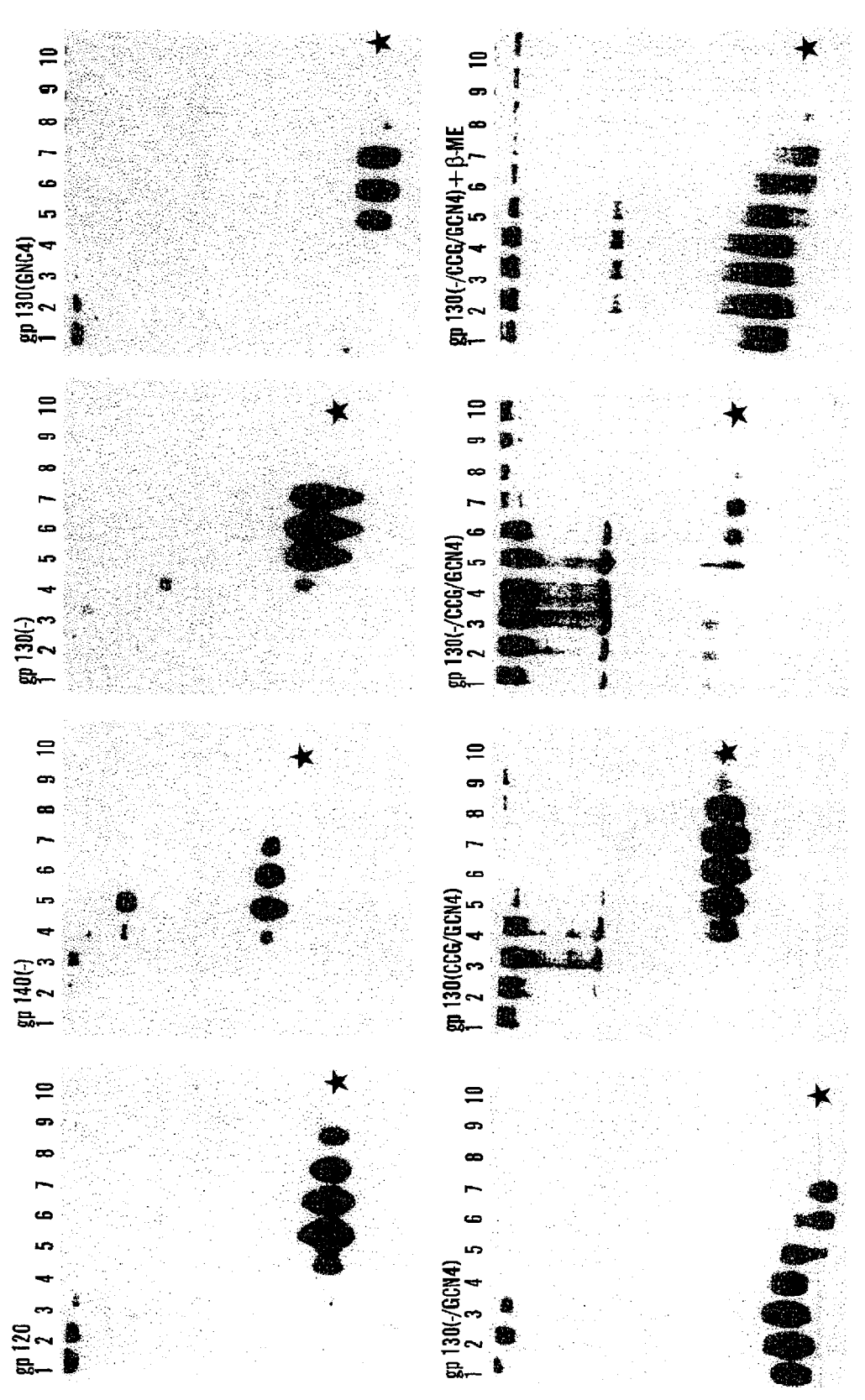

Radiolabeled envelope glycoproteins were produced transiently in transfected 293T cells supernatants, which were concentrated and analyzed by sucrose density gradient centriftigation. Gradient fractions were collected and precipitated by a mixture of sera from HIV-1-infected individuals. The immunoprecipitates were analyzed on SDS-polyacrylamide gels under reducing and non-reducing conditions. Autoradiographs of some of these gels are shown in FIG. 2A. The gp120 glycoprotein, which is known to be monomeric, sedimented primarily in fractions 5–7 of the gradient. A small amount of the gp120 glycoprotein was found in fractions 1–3 and migrated on the non-reducing gels as high molecular weight forms. These slowly migrating forms of gp120 were not observed on reducing gels (data not shown) and probably represent previously described, aberrantly cross-linked envelope glycoproteins (Owens, R. J. and R. W. Compans, *Virology* 179: 827–33, 1990). The gp140(−) glycoprotein exhibited mostly monomeric forms that sedimented in fractions 5–7, although some presumed gp140(−) dimers and high order forms were observed in fractions 4–6 and 24, respectively. Likewise, the gp130(−) glycoprotein sedimented mostly as a monomer in fractions 5–7, although higher order forms could be seen in fractions 24. The gp130(GCN4) glycoprotein sedimented similarly to the gp130(−) glycoprotein. The majority of the gp130 (GCN4) glycoprotein sedimented as a monomer in the sucrose gradient (fractions 5–7) and migrated with an apparent molecular weight of approximately 120 kD. The small portion of the gp130(GCN4) glycoprotein that sedimented more rapidly (fractions 1–3) exhibited two molecular weights (approximately 130 kD and greater than 350 kD) on non-reducing SDS-polyacrylamide gels. This pattern suggests that uncleaved gp130(GCN4) is oligomeric, whereas the proteolytically cleaved gp130(GCN4) glycoprotein is monomeric. That the lack of cleavage between the gp120 and gp41 moieties stabilizes the oligomer is supported by the sedimentation pattern of the gp130(−/GCN4) glycoprotein. The majority of this protein sedimented in fractions 1–4, with the proteins in these fractions exhibiting molecular weights of 130 and greater than 350 kD. A small portion of the gp130(−/GCN4) glycoprotein was cleaved to a form of approximately 120 kD, which sedimented as a monomer in fractions 5–8. Thus, the faster-sedimenting fractions of the gp130(GCN4) and gp130(−/GCN4) glycoproteins, which presumably represent higher-order oligomers, contain only uncleaved proteins.

To determine if potential intersubunit disulfide bonds could be formed and if these might contribute to trimer stability, the gp130(CCG/GCN4) and gp130(−/CCG/GCN4) proteins were studied. The gp130(CCG/GCN4) glycoprotein sedimented similarly to the gp130(GCN4) glycoprotein, with a substantial portion of the protein present in fractions 5–7 and a portion of the protein in fractions 1–4. As was seen for the gp130(GCN4) glycoprotein, the more slowly sedimenting fractions consisted mainly of an apparently cleaved gp120 glycoprotein. The faster sedimenting portion of the gp130(CCG/GCN4) protein exhibited a molecular weight of greater than 350 kD under non-reducing conditions. Unlike the case for the gp130(GCN4) protein, no 130 kD band was prominent in fractions 1–3 of the gp130(CCG/GCN4) protein. This indicates that the substitution of the cysteine pair in the gp41 ectodomain resulted in covalent cross-linking of some of the gp130(CCG/GCN4) envelope glycoprotein subunits. The vast majority of the gp130(−/CCG/GCN4) glycoprotein sedimented in fractions 1–5 and migrated with an apparent molecular weight of greater than 350 kD. A portion of these high molecular weight glycoproteins could be reduced by the treatment with 1.5% β-mercaptoethanol (β-ME), and interestingly, these reduced products of the gp130(−/CCG/GCN4) oligomer consisted almost exclusively of the uncleaved 130 kD glycoprotein (bottom right panel of FIG. 2A). A small amount of the gp130(−/CCG/GCN4) was apparently cleaved and sedimented in fractions 5–8, consistent with a gp130 monomer. Almost all of the greater than 350 kD forms of the gp130(CCG/GCN4) and gp130(−/CCG/GCN4) glycoproteins could be reduced by boiling in 5% β-ME to proteins of 130 kD apparent molecular weight (see FIG. 2C below).

These results demonstrate that the inclusion of GCN4 sequences and the disruption of proteolytic cleavage contribute to the formation and stabilization of soluble, higher-order oligomers. The presence of the cysteine pair in the gp41 coiled coil allows intersubunit disulfide bonds to form, covalently stabilizing these oligomers.

Immunoprecipitation of Soluble HIV-1 Envelope Glycoproteins.

Figure 2B:
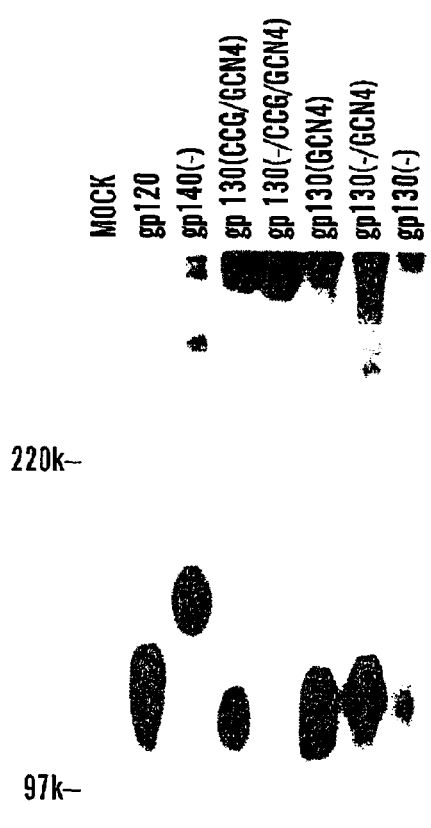

The radiolabeled supernatants containing the soluble HIV-1 envelope glycoprotein variants were also studied by direct immunoprecipitation by a mixture of sera from HIV-1-infected individuals. The precipitates were analyzed on SDS-polyacrylamide gels run under non-reducing conditions (FIG. 2B). The results indicate that, under these conditions, the glycoproteins with the cysteine pair (gp130 (CCG/GCN4) and gp130(−/CCG/GCN4)) exhibited the greatest proportion of high molecular weight forms. Consistent with the results from the sucrose gradients, the low molecular weight species of the gp130(CCG/GCN4) protein appears to be a cleaved gp120. The vast majority of the gp130(−/CCG/GCN4) protein migrated as a high molecular weight species, underscoring the efficacy of the cysteine cross-linking in this context. This higher order form of the gp130(−/CCG/GCN4) glycoprotein migrated on SDS-polyacrylamide gels at a molecular weight of approximately 400 kD, which was determined by comparing its migration with those of protein molecular weight markers and envelope glycoproteins oligomers of known sizes (Farzan, M., et al., J. Virol. 72: 7620–5, 1998) (FIG. 2B). This estimated molecular weight was consistent with the notion that the gp130(−/CCG/GCN4) glycoprotein forms a trimer. The gp130(−/GCN4) protein migrated primarily as a 130 kD product, although some higher molecular weight forms were evident. Consistent with proteolytic cleavage, the gp130 (GCN4) protein migrated as 130 and 120 kD species. The gp140(−) migrated primarily as a 140 kD protein, although high molecular weight forms consistent with dimers, trimers and other higher-order forms could be discerned. No high molecular weight species of the gp120 glycoprotein were evident.

Figure 2C:

To demonstrate that disulfide bond formation contributed to the stabilization of oligomers, the precipitated gp130 (CCG/GCN4) and gp130(−/CCG/GCN4) glycoproteins were boiled in the presence of β-ME prior to analysis on SDS-polyacrylamide gels (FIG. 2C). Boiling for 3 minutes in 1.5% β-ME resulted in partial disruption of the higher molecular weight forms of these glycoproteins. Boiling for 10 minutes in 5% β-ME almost completely reduced the gp130(CCG/GCN4) and gp130(−/CCG/GCN4) oligomers to lower molecular weight forms. The majority of the monomeric forms produced upon reduction of both these proteins migrated as a 130 kD species, consistent with the idea that lack of proteolytic cleavage promotes trimer stability. These results indicate that the gp130(CCG/GCN4) and gp130(−/CCG/GCN4) glycoproteins maintain the higher-order forms on SDS-polyacrylamide gels through the formation of disulfide bonds.

Recognition of Soluble Envelope Glycoproteins by the DP178 gp41 Peptide.

Figure 3:
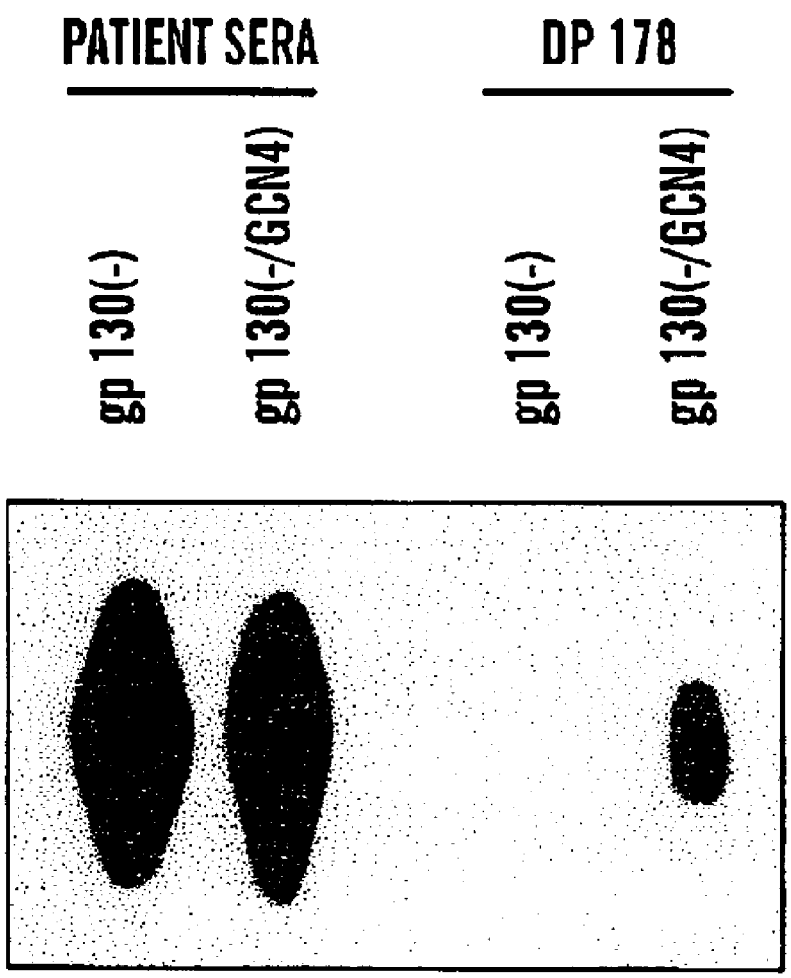

The cross-linking of the soluble envelope glycoprotein subunits by cysteines placed at the internal d and e positions of the gp41 heptad repeat implies that at least part of the N-terminal helical coiled coil can be formed in these proteins. To examine this further, we asked whether the DP178 peptide, which corresponds in sequence to the C-terminal α-helix of the gp41 ectodomain (C34 in FIG. 1), could interact with the soluble trimers. The DP178 peptide forms a helix that packs into a hydrophobic groove formed on the outer surface of the N-terminal gp41 coiled coil (Chen, C. H., et al., J. Virol. 69: 3771–7, 1995). The $^{35}$S-Met/Cys-labeled supernatants, which were adjusted to contain the same amounts of the gp130(−) and gp130(−/GCN4) glycoproteins, were precipitated by either a mixture of sera from HIV-1-infected individuals or the PK-C299 peptide/1D4 antibody mixture. The PK-C299 peptide is composed of the DP178 HIV-1 gp41 sequence fused to a C9 peptide tag corresponding to the C-terminus of bovine rhodopsin. The C9 peptide epitope is recognized by the 1D4 antibody. Equivalent amounts of the gp130(−) and gp130(−/GCN4) glycoproteins were precipitated by the mixture of sera from HIV-1-infected individuals (left panel, FIG. 3). The gp130 (−/GCN4) glycoprotein was precipitated much more efficiently than the gp130(−) glycoprotein by the PK-C399/1D4 antibody mixture (right panel, FIG. 3). Thus, the soluble gp130(−/GCN4) glycoprotein, which forms stable trimers, can be recognized more efficiently by the DP178 peptide than a similar glycoprotein that is primarily monomeric.

Recognition of the Soluble HIV-1 Envelope Glycoproteins by Antibodies.

Figure 4A:
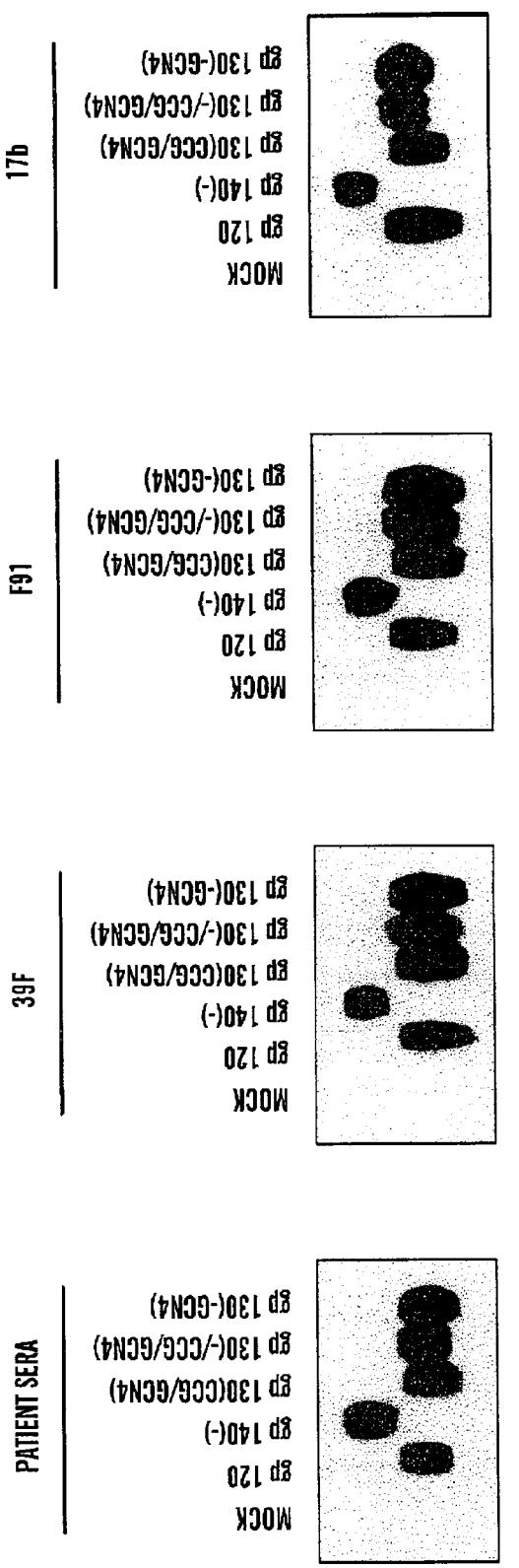

The structural integrity of three of the soluble glycoproteins (gp130(CCG/GCN4), gp130(−/CCG/GCN4) and gp130(−/GCN4)) that exhibited some trimeric forms was demonstrated by precipitation by a panel of antibodies directed against different epitopes on the HIV-1 envelope glycoproteins. The soluble gp120 and gp140(−) glycoproteins, which are mainly monomeric, were included in this study for comparison. Radiolabeled supernatants containing similar levels of all five glycoproteins were precipitated by either a mixture of sera from HIV-1-infected individuals or by a monoclonal antibody. Precipitates were analyzed on SDS-polyacrylamide gels after complete reduction in 5% β-ME. FIG. 4A shows that the mixture of HIV-1-infected patient sera precipitated similar levels of all five glycoproteins. The gp130(CCG/GCN4) glycoprotein migrated as proteolytically cleaved gp120 and uncleaved gp130 forms. The recognition patterns of the 39F, 17b and F91 antibodies were similar to that of the mixture of sera. The 39F antibody recognizes a conformation-dependent structure in the third variable (V3) loop of the HIV-1 gp120 glycoprotein (J. Robinson, personal communication). The 17b antibody binds to a discontinuous gp120 epitope that is induced by CD4 binding and that overlaps the conserved chemokine receptor-binding region. The 48d antibody, which recognizes a related, overlapping epitope, was also tested and exhibited a similar pattern of recognition (data not shown). The F91 antibody recognizes a discontinuous gp120 epitope overlapping the CD4 binding site. Two other antibodies directed against CD4 binding site (CD4BS) epitopes on gp120, F105 and IgG1b12, were also tested and exhibited similar recognition profiles (data not shown). These results suggest that the discontinuous epitopes recognized by several anti-gp120 monoclonal antibodies are present and accessible on the soluble trimers. These results were confirmed when the rapidly sedimenting fractions of the gp130 (CCG/GCN4), gp130(−/CCG/GCN4) and gp130(−GCN4) proteins were first prepared on sucrose gradients and then immunoprecipitates (data not shown).

Figure 4B:
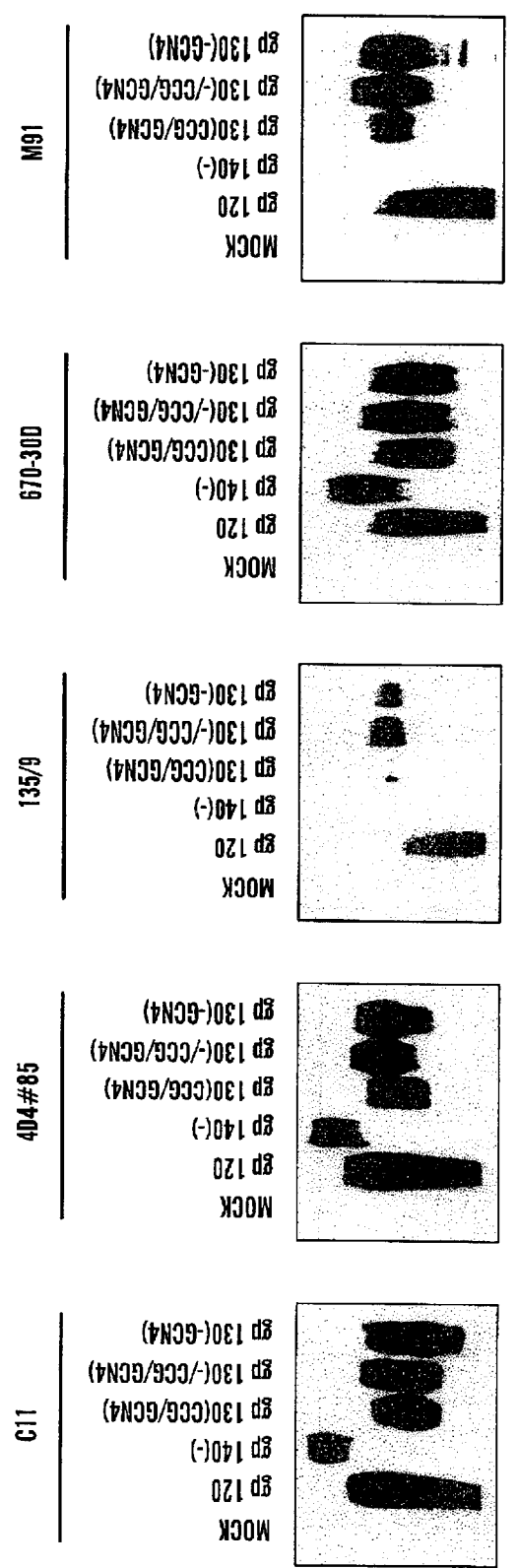

It has been suggested that the first (C1) and fifth (C5) conserved regions of the HIV-1 gp120 envelope glycoprotein, which are located in the N- and C-termini, respectively, of the glycoprotein, are involved in the interaction with the gp41 ectodomain (Dalgleish, A. G., et al., Nature 312: 763–7, 1984; Helseth, E., et al., J. Virol. 65:2119–23, 1991; Wyatt, R., et al., J. Virol. 71: 9722–31, 1997). To investigate the integrity and accessibility of gp120 epitopes from these regions on the soluble envelope glycoproteins, the radiolabeled glycoproteins were precipitated by antibodies that recognize epitopes with C1 and/or C5 components (FIG. 4B).

The C11 antibody, which recognizes a discontinuous gp120 epitope composed of C1 and C5 elements, was able to precipitate all five of the soluble envelope glycoproteins. However, there were some qualitative and quantitative differences between the recognition pattern of the C11 antibody and those of the antibodies described above. As reported previously (52), the gp140(−) glycoprotein was recognized by the C11 antibody less efficiently than the soluble gp120 glycoprotein, in contrast to the recognition pattern observed for the mixture of sera from HIV-1-infected individuals. The proteolytically cleaved, monomeric forms of the gp130 (CCG/GCN4), gp130(−/CCG/GCN4) and gp130(−/GCN4) glycoproteins were more efficiently precipitated by the C11 antibody than by the serum mixture. The efficient precipitation of the gp130(−/CCG/GCN4) and gp130(−/GCN4) monomers by the C11 antibody was particularly noteworthy because proteolytically cleaved monomers represented only a small fraction of these two glycoprotein preparations. Although the trimeric, uncleaved forms of these glycoproteins could be precipitated by the C11 antibody, the precipitation of these forms was relatively less efficient than that observed for the previously discussed antibodies. These results suggest that the C11 antibody can access the gp130 trimers, but binds less efficiently to the trimers than to the gp120 monomer. This impression was confirmed by precipitation of monomers and trimers prepared on sucrose density gradients (data not shown).

The 522-149, #45 and M90 antibodies, which are directed against discontinuous C1 gp120 epitopes, precipitated the uncleaved gp130 glycoproteins efficiently (data not shown). Similar results were obtained with the A32 antibody, which recognizes a discontinuous C1–C4 gp120 epitope (data not shown). As previously reported (Wyatt, R., et al., J. Virol. 71: 9722–31, 1997), the efficiency with which the gp140(−) glycoprotein was precipitated by these antibodies was somewhat decreased relative to that observed for the mixture of sera from HIV-1-infected individuals (data not shown).

The recognition of the soluble glycoproteins by antibodies that bind linear HIV-1 gp120 epitopes in the C1 region was also examined. The 4D4#85 antibody, which recognizes an epitope within residues 35–50 of gp120, efficiently precipitated the gp120, gp130(CCG/GCN4), gp130(−/CCG/GCN4), and gp120(−/GCN4) glycoproteins and precipitated the gp140(−) glycoprotein less efficiently (FIG. 4B). The 133/290 and 135/9 antibodies recognize epitopes that span gp120 residues 61–70 and 111–120, respectively (Moore, J. P., and J. Sodroski, J. Virol. 70 1863–72, 1996). These antibodies only inefficiently precipitated faster-migrating, presumably under-glycosylated forms of the HIV-1 gp120 glycoprotein (FIG. 4B and data not shown), consistent with earlier studies indicating the poor exposure of these linear epitopes on native gp120 (Helseth, E., et al., J. Virol. 64: 6314–8, 1990). The gp140(−) glycoprotein was not precipitated by these antibodies. The 133/290 and 135/9 antibodies precipitated only the uncleaved, trimeric forms of the gp130 glycoprotein variants (FIG. 4B and data not shown). The monomeric, cleaved forms of the gp130 glycoproteins were not recognized by these antibodies. The tendency of the 133/290 and 135/9 antibodies to precipitate the trimeric forms of the gp130(−/CCG/GCN4) and gp130(CCG/GCN4) glycoproteins preferentially over monomeric forms was even more pronounced when sucrose density-purified fractions of these proteins were tested (data not shown).

The recognition of the soluble glycoproteins by antibodies that bind linear gp120 epitopes in the C5 region was also examined. The 670-30D antibody, which recognizes an epitope encompassing gp120 residues 498–504, precipitated all five proteins efficiently (FIG. 4B) (Zolla Pazner, S., et al., J. Virol. 69: 3807–15, 1995). A similar result was obtained with the 1331A antibody, which is directed against the same C5 region (data not shown). The M91 and CRA-1 antibodies recognize gp120 residues 461–470, which span the boundary of the V5 and C5 regions (Moore, J. P. and J. Sodroski, J. Virol. 70: 1863–72, 1996). These antibodies precipitated only faster migrating, presumably less glycosylated forms of soluble gp120, consistent with previous studies indicating that native gp120 is not recognized efficiently by these antibodies (Moore, J., et al., J. Virol. 68: 469–84, 1994). The gp140(−) glycoprotein was not precipitated by either antibody (FIG. 4B and data not shown). The M91 and CRA-1 antibodies preferentially recognized the trimeric, uncleaved forms of the gp130 glycoproteins. This preference was confirmed by precipitation of monomeric and trimeric preparations of these glycoproteins purified on sucrose gradients (data not shown).

The extension of the N-terminal gp41 coiled coil by a coiled coil such as the trimeric GCN4 sequence was preferable for the efficient production of stable, soluble trimers (FIG. 5). The success of this approach suggests that, within the trimers, elements of the N-terminal coiled coil are formed and participate in intersubunit contacts. This assertion is supported by the observation that intersubunit disulfide bonds form when cysteines are placed in the d and e positions of the N-terminal gp41 heptad repeat (Farzan, M., et al., J. Virol. 72: 7620–7625, 1998). These positions are located on the inner, hydrophobic face of the coiled coil and are separated by distances that are acceptable for disulfide bond formation (Chan, D. C., et al., Cell 89: 263–73, 1997; Tan, K., et al., Proc. Natl. Acad. Sci. USA 94: 12303–8, 1997; Weissenhom, W., et al., *Nature* 387: 426–30, 1997). That the N-terminal gp41 coiled coil is well formed along its length in the soluble gp130 trimers is supported by the ability of DP178, which corresponds to the C-terminal α-helix in the gp41 ectodomain, to bind these oligomers. C-terminal α-helical gp41 peptides have been shown to bind within a long hydrophobic groove created by the interaction of two N-terminal gp41 helices in the coiled coil (Chan, D. C., et al., *Proc. Natl. Acad. Sci. USA* 95: 15613–7, 1998). The accommodation of the N-terminal gp41 coiled coil within a stable, soluble trimer indicates this coiled coil exists, at least in part, within the complete HIV-1 envelope glycoprotein precursor and contributes to oligomerization. Disulfide bonds among the trimer subunits form as a result of the introduction of the cysteine pair at positions 576 and 577 of the complete HIV-1 gp160 envelope glycoprotein precursor, further supporting this model (Farzan, M., et al., *J. Virol.* 72: 7620–7625, 1998). Perhaps the coiled coil of the HIV-1 fusion protein, unlike that of the influenza virus, does not need to undergo extensive conformational changes from a precursor state in order to form (Bullough, P. A., et al., *Nature* 371: 337–43, 1994).

The second factor that exhibited a major influence on the stability of soluble HIV-1 envelope glycoprotein trimers was proteolytic cleavage at the gp120-gp41 junction (FIG. 5). Regardless of the means by which the trimer subunits-were associated, including the presence of covalent disulfide bonds in the gp41 subunit, cleaved proteins were monomeric. This was unexpected because at least a portion of the cleaved, membrane-associated HIV-1 envelope glycoproteins retains trimeric structure on native virions. The basis for this difference is unknown, but it may simply reflect the greater lability of soluble envelope glycoprotein trimers or, alternatively, might be due to differences in the accommodation of the cleaved segments in the two contexts.

In the case of the gp130(−/GCN4) and gp130(−/CCG/GCN4) glycoproteins, a low level of proteolytic cleavage was observed despite alteration of two basic residues N-terminal to the cleavage site. It is uncertain whether cleavage occurred precisely at the natural site in these mutants, although the recognition of the cleaved gp120 glycoprotein by antibodies against gp120 C-terminal regions was comparable to that of wild-type gp120. Efforts to reduce the observed residual cleavage by further alteration of basic residues near the natural cleavage site did not succeed (data not shown).

Covalent linkage of the trimeric subunits through disulfide bond formation (FIG. 5) resulted in extremely stable oligomers that remained associated on SDS-polyacrylamide gels run under non-reducing conditions or in the presence of 1.5% β-ME. Although covalent linkage was neither necessary nor sufficient for the production of stable soluble trimers, it should prove useful in circumstances where trimers are subjected to harsh conditions.

During natural infection, the humoral response to the HIV-1 envelope glycoproteins consists of both non-neutralizing and neutralizing antibodies. Many of the non-neutralizing antibodies appear to be generated against shed, monomeric gp120 glycoproteins and do not bind efficiently to the functional envelope glycoprotein trimer (Parren, P. W., et al., *Nature Med.* 3: 366–7, 1997). The vast majority of the gp120 epitopes, including all of the neutralization epitopes examined, were present on the soluble gp130 trimers and exposed similarly to that seen on the monomeric gp120 glycoprotein. Differences between monomeric and trimeric envelope glycoproteins involved epitopes in the first (C1) and fifth (C5) conserved regions of gp120, which have been previously implicated in the interaction with gp41. The C11 antibody, which recognizes a discontinuous gp120 epitope with C1 and C5 components, precipitated the proteolytically cleaved, monomeric forms of the soluble glycoproteins more efficiently than any of the other antibodies studied. This is consistent with the idea that the C11 antibody was generated to a monomeric, soluble gp120 glycoprotein shed from virions or infected cells during natural HIV-1 infection (Moore, J. P., and J. Sodroski, *J. Virol.* 70:1863–72, 1996).

Recognition of the gp130 proteins by some antibodies directed against linear C1 and C5 epitopes was actually increased relative to recognition of the gp120 or gp140(−) monomers. Previous studies of the native HIV-1 gp120 monomer suggested that C1 and C5 sequences at the very N- and C-terminus of the protein, respectively, were well exposed, whereas more interior N- and C-terminal residues were less accessible to antibodies (Moore, J., et al., *J. Virol.* 68: 469–484, 1994; Moore, J. P., and J. Sodroski, *J. Virol.* 70: 1863–72, 1996). This is consistent with the known involvement of the interior C1 and C5 sequences in secondary structural elements of the gp120 core domains (Kwong, P. D., et al., *Nature* 393: 648–659,1998). In our study, recognition of the mature, fully glycosylated gp120 monomer by antibodies against interior C1 regions (residues 61–70 and 111–120) and an interior C5 region (residues 461–470) was minimal (Moore, J. P., et al., *J. Virol.* 69: 101–109; 1995). By contrast, these regions were accessible to antibodies on the trimeric, but not the monomeric, forms of the soluble gp130 glycoproteins. These observations suggest that, in the formation of these trimers, the N- and C-terminal regions of gp120 are extended into more exposed conformations than those assumed in the gp120, gp140 and gp130 monomers. Interestingly, the influenza $HA_1$ glycoprotein N- and C-termini, which make extensive contacts with the $HA_2$ transmembrane protein, also exhibit extended structures in the trimeric hemagglutinin complex (Chen, J., et al., *Cell* 95: 409–17, 1998).

Another explanation for the differential recognition of the monomers and trimers by the C1-directed antibodies, 133/290 and 135/9, and by the C5-directed antibodies, M91 and CRA-1, is a potential difference in the glycosylation of monomeric and trimeric soluble glycoproteins. Although these antibodies did not recognize the fully glycosylated gp120 monomer, they did precipitate a faster-migrating form of gp120 that is presumably incompletely glycosylated. It is possible that soluble trimers are glycosylated differently than the monomeric proteins, contributing to better recognition by these antibodies.

Surprisingly, the formation of stable gp130 trimers was not sufficient to render all of the non-neutralizing gp120 epitopes inaccessible to antibodies. In fact, the linear C1 and C5 epitopes that are accessible only on the soluble gp130 trimers are not thought to be available for antibody binding in the context of the functional virion spike and, consequently, are not neutralization targets. Some of these differences between soluble gp130 glycoproteins and membrane-associated, native envelope glycoprotein trimers may be due to the presence of the glycosylated, C-terminal portion of the gp41 ectodomain or the viral membrane in the latter. Alternatively, the soluble gp130 glycoproteins may be trapped in a different conformation than that normally assumed by the envelope glycoproteins on the virion spike. However, we believe that the conformation of our trimer is similar to that of the wild type virus.

EXAMPLE 2

Stabilization of Variable-loop Deleted Soluble Trimers by the GCN4 Coiled-coil Motif In one preferred method of immunization one would prime with a trimer having variable loop-deleted gp120, and then boost with a trimer that more closely approximates the wild type viral glycoprotein until at least one final boost with the stabilized wild type trimer. For example, if multiple variable regions and sugar addition sites are deleted from the priming trimer, the next boost will be with a trimer where more variable region amino acids are present and/or sugar addition sites present. Each boost will get closer to the wild type configuration until that configuration is reached.

FIG. 7 shows that variable loop-deleted HIV-1 proteins are still trimeric. These proteins are based upon gp140 (see FIG. 1) where the V1 and V2 variable loops have been deleted (−V1/V2) and replaced with the sequence Gly-Gly-Gly. The GCN4 coiled coil is inserted at the carboxyl terminus. The resulting gp140−−V1/V2 is still trimeric as is the wild type gp140 (wt). Both are referred to as gp140T-−V1/V2 and gp140 T-wt, respectively. The monomer is referred to as gp140M.

EXAMPLE 3

Elicitation of Neutralizing Antibodies Against Primary HIV by Soluble Stabilized Envelope Glycoprotein Trimers Materials and Methods Plasmids. Details of the plasmids expressing soluble, stabilized trimers have been previously reported (Yang, X. et al., *J. Virol.* 74: 4746–4754, 1999; Yang, X. et al., *J. Virol.* 74: 5716–5725, 2000). Briefly, all plasmids were derivatives of the pSVIIIenv vector (Sullivan, et al., *J. Virol.* 69: 4413–4422, 1995). For production of soluble gp120 monomers, a stop codon was introduced into the env gene of the pSVIIIenv plasmid, resulting in termination after arginine 508 (amino acid residues are numbered according to the HXBc2 prototype). The gp120-gp41 proteolytic cleavage site was modified in the soluble, stabilized trimers by altering the arginines at residues 508 and 511 to serines. The GCN4 trimeric motif (MKQIEDKIEEILSKIYHIENEIARIKKLIGEV) (SEQ ID No:2) (Harbury et al., *Science* 262: 1401–7, 1993) was positioned after leucine 593 in the gp130(−/GCN4) construct, after lysine 675 in the gp140Δ675(−/GCN4) construct, and after lysine 683 and a pair of glycine residues in the gp140Δ683(−/GCN4) construct. The open reading frames of these constructs were sequenced in their entirety to confirm that only the desired changes had been introduced.

Protein expression and purification. Envelope glycoproteins were produced by transfection of forty 100 mm plates of 293T cells with the pSVIIIenv plasmid and another plasmid expressing the HIV-1 Tat protein, using Effectene™ reagents (Qiagen). The envelope glycoproteins were purified from the pooled supernatants using an F105 antibody affinity column as described (Kwong, P. D., et al., *J. Biol. Chem.* 274: 4115–4123, 1999; Wu, L., et al., *Nature* 184:179–83, 1996). The protein preparations were evaluated for purity and quantified by comparison with serial dilutions of bovine serum albumin after resolution on 7.5% SDS-polyacrylamide gels. The purified envelope glycoproteins were stored in aliquots at −20° C.

Immunization and serum preparation. The amounts of each envelope glycoprotein in the inoculum were adjusted so that each animal received the same molar quantity of the gp120 moiety, which is the major target for neutralizing antibodies (Berkower, I., et al., *J. Exp. Med.* 170 1681–1695, 1999; Haigwood, N. L., et al., *J. Virol.* 66:172–182, 1992; Matthews, T. J., *AIDS Res. Hum. Retroviruses* 10: 631–632, 1994; Profy, A. T., et al., *J. Immunol.* 144: 4641–4647, 1990; Steimer, K. S., et al., *Science* 254: 105–8, 1991; Van Cott, T. C., et al., *J. Virol.* 71: 4319–4330, 1997; Van Cott, T. C., et al., *J. Virol.* 73: 4640–4650, 1999; Wyatt, R., and J. Sodroski, *Science* 280: 1884–1888, 1998; Wyatt, R., et al., *Nature* 393: 705–711, 1998). Thus, the following amounts of each protein were added to 200 microliters (final volume) of a solution containing 1×Ribi adjuvant (Sigma): 6.8 µg YU2 gp120, 7.8 µg YU2 gp130(−/GCN4), 9.0 µg YU2 gp140Δ675(−/GCN4) or gp140Δ683(−/GCN4), 6.5 µg HXBc2 gp120 and 9.0 µg HXBc2 gp140Δ675(−/GCN4). As controls, 9.0 µg of bovine serum albumin (BSA) or PBS alone was inoculated. Groups of at least six Balb/c female mice (Taconic) were inoculated subcutaneously with 200 microliters of the immunogen solutions at three separate sites. Inoculations were administered at the ages of 9, 13 and 17 weeks. Eye bleeding was performed at 7 and 14 days after the third injection. Following clot formation for 24 hours at 4° C., the samples were centrifuged at 14,000 rpm for 10 minutes at room temperature and the sera harvested in a sterile manner. The two serum samples from each mouse were pooled and incubated at 55° C. for one hour to inactivate complement. The sera were then stored at 4° C.

HIV-1 neutralization assay. The HIV-1-neutralizing activity of the serum samples was tested using a single-round virus entry assay. Recombinant HIV-1 expressing the firefly luciferase gene was produced by transfecting 293T cells with the pCMV Gag-Pol packaging construct and the pHIV-luc vector, along with a pSVIIIenv plasmid expressing the envelope glycoproteins of different HIV-1 strains (Koch, M., et al., manuscript submitted; Sullivan, et al., *J. Virol.* 69: 4413–4422, 1995). Two days after transfection, the cell supernatants were harvested and frozen in aliquots as viral stocks.

To create target cells, $2.5 \times 10^6$ Cf2Th canine thymocytes were transfected using Lipofectamine PLUS™ (Gibco Lifetech, Inc.) with 5 µg each of plasmids expressing human CD4 and either human CCR5 or CXCR4, as appropriate for the infecting virus (Choe, H., et al., *Cell* 85: 1135–48). After culturing overnight, the transfected cells were detached from the plates using 10 mM EDTA/PBS. After washing in PBS, $6 \times 10^3$ cells were distributed into each well of a 96-well cell culture plate (Dynex). After overnight incubation, the cells were used for infection.

To quantify the infectivity of each viral stock, different amounts of the stocks were diluted to 200 µl using growth medium and incubated at 37° C. for one hour. Growth medium was thoroughly removed from the target cells and 50 µl of the virus suspension was added to triplicate wells. The virus-cell mixture was incubated at 37° C. in 5% $CO_2$ for two hours, after which the medium was aspirated and the cells washed once with 200 µl of pre-warmed growth medium per well. After aspiration of the medium, another 200 µl of growth medium was added, and the cells were cultured for two days. At this time, luciferase activity was measured using the luciferase assay system (Pharmingen). Any values more than 200% above or less than 50% below the median value of triplicates were excluded from calculation of the mean infectivity titer. In practice, less than 10% variation was observed for the infectivity of viral stocks within an experiment. The linear range of the assay extended from 50 to $2 \times 10^5$ arbitrary luciferase units (data not shown).

In the neutralization assays, an amount of viral stock sufficient to result in luciferase activity of approximately $1 \times 10^5$ units was diluted to 50 µl in DMEM/10% FBS. The mouse sera were diluted in the same medium and the final volume adjusted to 150 µl. The virus and sera were then mixed, briefly vortexed, and incubated in a 37° C., 5% $CO_2$ incubator for one hour. The residual viral infectivity was then measured in the single-round infection assay as described above. The reported serum titers represent the dilution of the serum in the final virus/serum mixture that resulted in either 50 or 90 percent neutralization, compared with the infectivity of viruses incubated with medium alone.

Measurement of anti-gp120 reactivity of sera. To quantitate anti-gp120 reactivity in the sera, 15 ng of the YU2 or HXBc2 gp120 glycoprotein produced in Drosophila cells (Kwong, P. D., et al., *J. Biol. Chem.* 274: 41 154123, 1999, Wu, L., et al., *Nature* 184:179–83, 1996) was adsorbed onto the well of an ELISA plate (Costar) for one hour. After blocking the plates, 100 of serially diluted serum from mice immunized with envelope glycoproteins from the homologous strain were applied to each well for one hour. After consecutive incubation with biotinylated anti-mouse IgG (Sigma) and streptavidin-horseradish peroxidase (Pierce), the plates were vigorously washed and developed by the TMB peroxidase substrate kit (Bio-Rad). A well was classified as positive if the value was greater than 200% of the average values observed in the four wells that were incubated with the dilution buffer only. These negative controls exhibited a standard deviation of no more than 20% of the mean value.

Results

Soluble Stabilized Envelope Glycoprotein Trimers.

Figure 9:
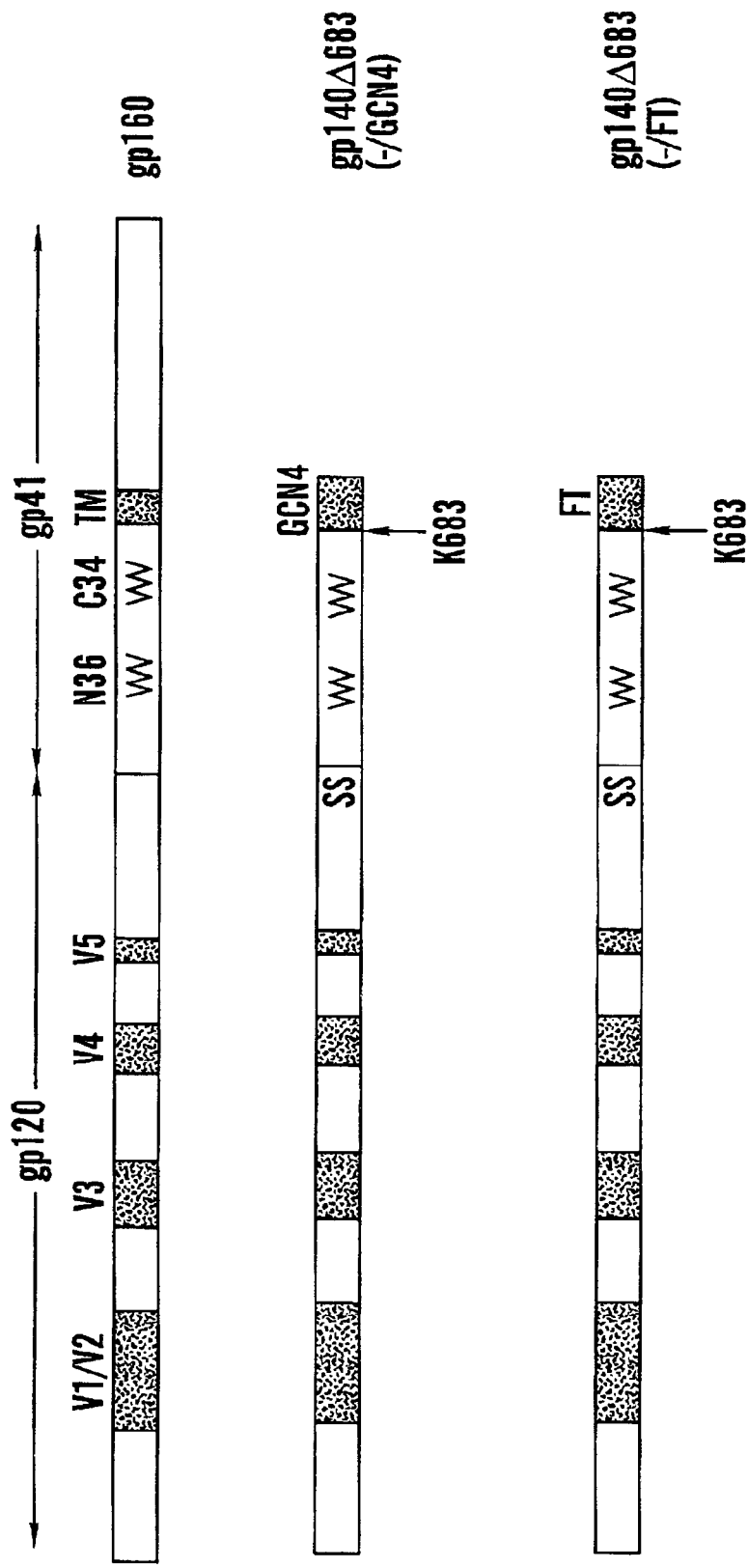

To create soluble forms of the HIV-1 envelope glycoproteins, the proteins were truncated at various locations within the gp41 ectodomain. In addition, the natural cleavage site between the gp120 and gp41 glycoproteins was altered to minimize proteolytic processing at this site (FIG. 9). Although these two modifications result in soluble envelope glycoproteins, such proteins exhibit considerable heterogeneity, forming monomers, dimers, tetramers and other oligomers (Earl, P. L., et al., *J. Virol.* 68: 3015–3026, 1994, Earl, P. L., et al., *Proc. Natl. Acad. Sci. USA* 87: 648–652, 1990). To promote the formation of soluble trimers, a sequence from the GCN4 transcription factor that was modified to form trimeric coiled coils (Harbury et al., *Science* 262: 1401–7, 1993) was appended to the carboxyl terminus of the soluble envelope glycoproteins (Yang, X. et al., *J. Virol.* 74: 4746–4754, 1999; Yang, X. et al., *J. Virol.* 74: 5716–5725, 2000). Three constructs that differ in the location of the carboxyl terminus, gp130(-/GCN4), gp140Δ675(-/GCN4), and gp140Δ683(-/GCN4), were studied. All three soluble glycoproteins assemble into relatively homogeneous, stable trimers (Yang, X. et al., *J. Virol.* 74: 4746–4754, 1999; Yang, X. et al., *J. Virol.* 74: 5716–5725, 2000). The antibody-accessible surface of the latter two trimers closely resembles that expected for the virion envelope glycoprotein complex (Yang, X. et al., *J. Virol.* 74: 5716–5725, 2000).

Soluble, stabilized trimers derived from two different clade B HIV-1 strains were expressed in a human cell line and purified to greater than 95 per cent homogeneity. The two strains were chosen to represent the extremes of phenotypic variation exhibited by HIV-1 isolates. The YU2 primary strain of HIV-1 was not passaged in tissue culture prior to molecular cloning (Li, Y., et al., *J. Virol.* 65: 3973–3985, 1991). This CCR5-using virus is one of the most difficult HIV-1 isolates to neutralize with antibodies or soluble forms of the CD4 receptor, and often demonstrates significant enhancement by these ligands (Sullivan, et al., *J. Virol.* 69: 4413–4422, 1995, Sullivan, N., et al., *J. Virol.* 72: 6332–6338, 1998). The TCLA HXBc2 strain of HIV-1, by contrast, utilizes CXCR4 as a coreceptor and is extremely sensitive to antibody-mediated neutralization (Sullivan, et al., *J. Virol.* 69: 4413–4422, 1995).

Mouse Immunization and Neutralization Assay

The immunogenicities of the soluble, stabilized trimers and gp120 monomers were compared in mice. Previous studies have demonstrated that gp120 induces neutralizing antibodies active against clinical HIV-1 isolates only after multiple immunizations, and then only at very low titers and with limited breadth (Barnett, S. W., et al., *Vaccine* 15: 869–873, 1997; Belshe, R. B., et al., *AIDS* 12: 2407–2415, 1998; Berman, P. W., et al., *Nature* 345: 622–625, 1990; Connor, R. I., et al., *J. Virol.* 72: 1552–76, 1998; Graham, B. S., et al., *J. Infect. Dis.* 177: 310–319, 1998; Haigwood, N. L., et al., *J. Virol.* 66:172–182, 1992; Mascola, J. R., et al., *J. Infect. Dis.* 173: 340–348, 1996; Rusche, J. R., et al., *Proc. Natl. Acad. Sci. USA* 84: 6924–6928, 1987; Van Cott, T. C., et al., *J. Virol.* 73: 4640–4650, 1999; and Wrin, T., and J. H. Nunberg, *AIDS* 8: 1622–1623, 1994). Nonetheless, as no other defined immunogen has proven consistently superior to gp120 in this respect, the use of gp120 as a point of comparison was reasonable (Berman, P. W., et al., *Nature* 345: 622–625, 1990; Klaniecki, J., et al., *AIDS Res. Hum. Retroviruses* 7: 791–798, 1991; Mascola, J. R., et al., *J. Infect. Dis.* 173: 340–348, 1996; Van Cott, T. C., et al., *J. Virol.* 71: 4319–4330, 1997). In this study, we utilized a conservative immunization protocol consisting of a priming inoculation followed by two boosts. At one and two weeks following the last boost, sera from the immunized mice were collected and assessed for virus-neutralizing activity. For this purpose, recombinant HIV-1 containing different envelope glycoproteins and expressing firefly luciferase were incubated with the sera and then used to infect canine thymocytes expressing CD4 and the appropriate chemokine receptor. The efficiency of this single round of infection was assessed by measurement of luciferase activity in the target cells two days after infection. This neutralization assay is quantitative, reproducible and relatively resistant to nonspecific effects of animal sera on the target cells. Three dade B HIV-1 envelope glycoproteins, YU2, ADA and HXBc2, were incorporated into the recombinant viruses used in the assay. The ADA primary isolate, like YU2, is resistant to neutralizing antibodies, whereas HXBc2 is quite sensitive to neutralizing antibodies (Sullivan, et al., *J. Virol.* 69: 4413–4422, 1995). This is reflected in the amounts of a highly potent neutralizing antibody, IgG1b12, required to inhibit recombinant viruses containing the three envelope glycoproteins (Burton, et al., *Science* 266: 1024–1027, 1994). Whereas 90% neutralization of the HXBc2 virus was observed in the presence of only 1.25:g/ml IgG1b12, the same degree of neutralization of the ADA and YU2 viruses could not be achieved by 10 and 20:g/ml IgG1b12, respectively. Approximately 50% neutralization of the ADA and YU2 viruses was observed at 2.5 and 5:g/ml IgG1b12, respectively (data not shown).

Neutralizing Antibodies Elicited by Primary HIV-1 Envelope Glycoproteins.

The immune responses to the YU2 envelope glycoprotein variants are summarized in Table 1. All of the envelope glycoproteins elicited roughly comparable titers of antibodies reactive with the homologous YU2 gp120 glycoprotein captured on an ELISA plate. None of the sera from mice immunized with the YU2 gp120 glycoprotein exhibited neutralizing activity against any of the viruses. By contrast, the soluble, stabilized YU2 trimers elicited neutralizing antibodies. The YU2 gp130(-/GCN4) and gp140Δ675(-/GCN4) glycoproteins generated serum responses that in some cases neutralized the heterologous viruses, but did not neutralize the homologous YU2 virus. This pattern of neutralization probably reflects the relative ease of neutralization of the three viruses (Sullivan, et al., *J. Virol.* 69: 4413–4422, 1995). The sera of several mice immunized with the YU2 gp140Δ683(-/GCN4) glycoprotein neutralized all three HIV-1 viruses. Four of six sera from this group of immunized mice mediated 90% neutralization of the YU2 virus at dilutions of 1:20 or greater; even 20:g/ml of the IgG1b12 antibody could not achieve this level of neutralization in this assay. These results indicate that the soluble, stabilized YU2 trimers, particularly the gp140Δ683(-/GCN4) glycoprotein, can elicit antibodies that neutralize primary HIV-1 isolates. In this respect, soluble, stabilized YU2 trimers appear to be significantly more effective than the monomeric YU2 gp120 glycoprotein.

To evaluate the breadth of neutralizing antibody responses elicited by the soluble, stabilized YU2 trimers, the sera were tested against recombinant viruses containing the envelope glycoproteins of primary HIV-1 isolates from clade B as well as clades C, D and E. Due to limitations in the amount of sera available, these experiments were performed at only one dilution (1:20). Again, the three soluble, stabilized YU2 trimers induced better neutralizing antibodies against the 89.6 and JR-FL viruses, two clade B HIV-1 strains, than the gp120 glycoprotein (data not shown). This neutralizing activity was weaker than that seen for viruses with the YU2 and ADA envelope glycoproteins. The gp140Δ683(−/GCN4) glycoprotein was not significantly different than the other two trimeric forms in the elicitation of neutralizing antibodies against the 89.6 and JR-FL strains. No neutralizing activity was observed against recombinant viruses containing the envelope glycoproteins from primary isolates outside of clade B (data not shown).

TABLE 1

Immune Responses following Immunization with Primary HIV-1 Envelope Glycoproteins

| Antigen | Mouse | Neutralizing Antibody Titers[a] | | | Anti-gp120 Reactivity[b] |
| --- | --- | --- | --- | --- | --- |
| | | YU2 | ADA | HXBc2 | |
| BSA | 34 | — | — | — | − |
| | 35 | — | — | — | − |
| | 36 | — | — | — | − |
| | 37 | — | — | — | − |
| | 38 | — | — | — | − |
| | 39 | — | — | — | − |
| YU2 gp120 | 1 | — | — | — | +++ |
| | 2 | — | — | — | ++++ |
| | 3 | — | — | — | +++ |
| | 4 | — | — | — | +++ |
| | 5 | — | — | — | ++ |
| | 6 | — | — | — | +++ |
| | 53 | — | — | — | + |
| | 54 | — | — | — | ++ |
| YU2 gp130 (—/GCN4) | 7 | — | — | 1:20 | +++ |
| | 8 | — | — | — | +++ |
| | 9 | — | — | 1:40 | +++ |
| | 10 | — | — | — | +++ |
| | 11 | — | 1:10 | 1:10 | +++ |
| | 12 | — | 1:10 | 1:10 | +++ |
| YU2 gp140Δ675 (—/GCN4) | 13 | — | 1:40 | 1:10 | +++ |
| | 14 | — | — | 1:20(1:20) | +++ |
| | 15 | 1:20 | 1:20 | 1:20 | ++++ |
| | 16 | — | 1:20 | 1:20 | +++ |
| | 17 | — | — | 1:10 | ++++ |
| | 18 | — | 1:20 | 1:10 | ++ |
| YU2 gp140Δ683 (—/GCN4) | 55 | >1:40(>1:40) | — | >1:20(1:10) | ++++ |
| | 56 | — | — | — | ++ |
| | 57 | 1:20(1:20) | 1:40 | 1:20(1:10) | ++++ |
| | 58 | 1:40 | 1:40 | 1:10 | +++ |
| | 59 | 1:20(1:20) | 1:40 | 1:10 | +++ |
| | 60 | 1:40(1:20) | 1:40 | 1:20 | +++ |

[a]The dilution of serum that resulted in at least 50% neutralization of recombinant viruses containing the indicated HIV-1 envelope glycoproteins is shown. A negative sign indicates that less than 50% inhibition was observed at a 1:10 dilution of the serum tested. The dilution of serum that resulted in at least 90% neutralization of the recombinant viruses is indicated in parentheses, when such neutralization was achieved.
[b]The reactivity of the serum with the YU2 gp120 glycoprotein captured on an ELISA plate is indicated. The scale is as follows: −, no signal at 1:2000 dilution; +, signal at 1:2000 dilution; ++, signal at 1:10,000 dilution; +++, signal at 1:50,000 dilution; and ++++, signal at 1:250,000 dilution.

Antibodies Elicited by TCLA HIV-1 Envelope Glycoproteins.

To examine whether the strain of the envelope glycoprotein immunogen can influence the results, mice were immunized with the gp120 and gp140Δ683(−/GCN4) glycoproteins derived from the HXBc2 TCLA HIV-1 strain. The HXBc2 trimers elicited more consistent neutralizing antibody responses than the HXBc2 gp120 glycoprotein (Table 2). However, this neutralizing activity was almost exclusively restricted to the homologous HXBc2 virus, and did not inhibit infection by the primary viruses, ADA and YU2. These results suggest that the strain from which the envelope glycoprotein components of soluble, stabilized trimers are derived can influence the efficiency with which neutralizing activity against clinical HIV-1 isolates is generated.

TABLE 2

Immune Responses following Immunization with TCLA HIV-1 Envelope Glycoproteins

| Antigen | Mouse | Neutralizing Antibody Titers[a] | | | Anti-gp120 Reactivity[b] |
| --- | --- | --- | --- | --- | --- |
| | | YU2 | ADA | HXBc2 | |
| HXBc2 gp120 | 22 | — | — | 1:10 | ++ |
| | 23 | — | — | 1:80(1:20) | ++ |
| | 24 | — | — | — | ++ |
| | 25 | — | — | — | − |
| | 26 | — | — | — | − |
| | 27 | — | — | — | + |
| HXBc2 gp140Δ675 (—/GCN4) | 28 | — | — | 1:80(1:40) | ++ |
| | 29 | — | — | 1:20(1:20) | ++ |
| | 30 | — | 1:10 | 1:80(1:40) | ++ |
| | 31 | — | — | 1:40(1:10) | + |
| | 32 | — | — | 1:10(1:10) | + |
| | 33 | — | — | 1:20(1:10) | ++ |

[a]Neutralizing antibody titers are reported as in Table 1.
[b]The reactivity of the serum with the HXBc2 gp120 glycoprotein captured on an ELISA plate is indicated. The scale is the same as that in Table 1. The sera from mice immunized with bovine serum albumin (BSA) did not exhibit reactivity with the captured HXBc2 gp120 glycoproteins (data not shown).

The development of an HIV-1 vaccine has been frustrated in part by the difficulty of eliciting neutralizing antibodies active against clinical HIV-1 isolates (Barnett, S. W., et al., Vaccine 15: 869–873, 1997; Beishe, R. B., et al., AIDS 12: 2407–2415, 1998; Berman, P. W., et al., Nature 345: 622–625, 1990; Connor, R. I., et al., J. Virol. 72: 1552–76, 1998; Graham, B. S., et al., J. Infect. Dis. 177: 310–319, 1998; Haigwood, N. L., et al., J. Virol. 6: 172–182, 1992; Mascola, J. R., et al., J. Infect. Dis. 173: 340–348, 1996; Matthews, T. J., AIDS Res. Hum. Refroviruses 10: 631–632, 1994; Rusche, J. R., et al., Proc. Natl. Acad. Sci. USA 84: 6924–6928, 1987; Van Cott, T. C., et al., J. Virol. 73: 4640–4650, 1999; Wrin, T., and J. H. Nunberg, AIDS 8: 1622–1623, 1994). To date, no defined immumunogen has proven better than the gp120 glycoprotein, which generates primary virus-neutralizing activity only after an aggressive immunization protocol involving many boosts (Barnett, S. W., et al., Vaccine 15: 869–873, 1997; Belshe, R. B., et al., AIDS 12: 2407–2415, 1998; Connor, R. I., et al., J. Virol. 72: 1552–76, 1998; Graham, B. S., et al., J. Infect. Dis. 177: 310–319, 1998; Haigwood, N. L., et al., J. Virol. 66: 172–182, 1992; Mascola, J. R., et al., J. Infect. Dis. 173: 340–348, 1996; Matthews, T. J., AIDS Res. Hum. Retroviruses 10: 631–632, 1994; Rusche, J. R., et al., Proc. Natl. Acad. Sci. USA 84: 6924–6928, 1987; Van Cott, T. C., et al., J. Virol. 73: 4640–4650, 1999). Immunization of specific transgenic mice with mixtures of cells expressing envelope glycoproteins and receptors has been reported to yield antibodies able to neutralize a broad range of primary HIV-1 isolates (LaCasse, R. A., et al., Science 283: 357–362, 1999); however, despite extensive effort, the relevant immunogen has not been defined and the reproducibility and general applicability of the results have not been demonstrated. Our results indicate that soluble, stabilized trimers are more effective than gp120 at eliciting antibodies that neutralize HIV-1. Such trimers may represent more faithful mimics of the functional envelope glycoprotein complex, may retain relevant conformations more stably in vivo, and can present multiple, cross-linked epitopes to responding B lymphocytes.

The HIV-1 strain from which the soluble, stabilized trimers are derived influences the elicitation of primary virus-neutralizing activity. The trimers derived from the primary YU2 isolate generated better neutralizing responses against clinical HIV-1 isolates than did trimers from a TCLA virus. This suggests that some primary virus trimers can elicit antibodies that recognize structures common to several primary and at least one TCLA HIV-1 isolate. The neutralizing antibodies generated by the TCLA virus trimer, although quite potent against the homologous TCLA isolate, were not generally active against the primary isolates tested. Despite the similarity of recognition of the YU2 and HXBc2 trimers by antibodies directed against conserved epitopes (Yang, X. et al., *J. Virol.* 74: 5716–5725, 2000), the neutralizing antibody response to the TCLA virus trimer appears to be dominated by reactivity with more strain-specific elements.

The YU2 gp140Δ683(-/GCN4) trimers, which contain the complete HIV-1 envelope glycoprotein ectodomains, raised antibodies that inhibited the YU2 virus, one of the primary HIV-1 isolates most resistant to antibody-mediated neutralization. The neutralizing activity of this sera, at 1:20 and 1:40 dilutions, was comparable in our assay to that of 5–20 µg/ml of the IgG1b12 antibody, one of the most potent HIV-1-neutralizing antibodies identified to date (Burton, et al., *Science* 266: 1024–1027, 1994). Thus, with the appropriate immunogen, neutralizing activity against even relatively refractory primary HIV-1 isolates is achievable using a conservative immunization protocol.

EXAMPLE 4

Stabilization of Soluble Stabilized Envelope Glycoprotein Trimers by the Fibritin Motif A variety of soluble HIV-1 envelope glycoprotein variants is shown in FIG. 9. The top panel is a schematic diagram of the main sequence and structure properties of HIV-1 gp160. The five variable loops of gp120 and the N36 and C34 helices of gp41 are marked. The construct of gp140 683(-/GCN4) has aGCN4 trimeric motif fused after amino acid 683 of gp160. To express gp140 683(-/FT) glycoprotein, the fibritin trimeric (FT) sequence of 'YIPEAPRDGQAYVRKDGEWVLLSTFL' (SEQ ID NO:4) was fused after amino acid 683 of gp160, just like in the gp140 683(-/GCN4) construct; and two glycine residues were inserted between the gp41 sequence and the fibritin sequence to allow some degree of structural flexibility of the final protein product. The cleavage site between gp120 and gp41 was also mutated to limit the protease cleavage.

Figure 10:
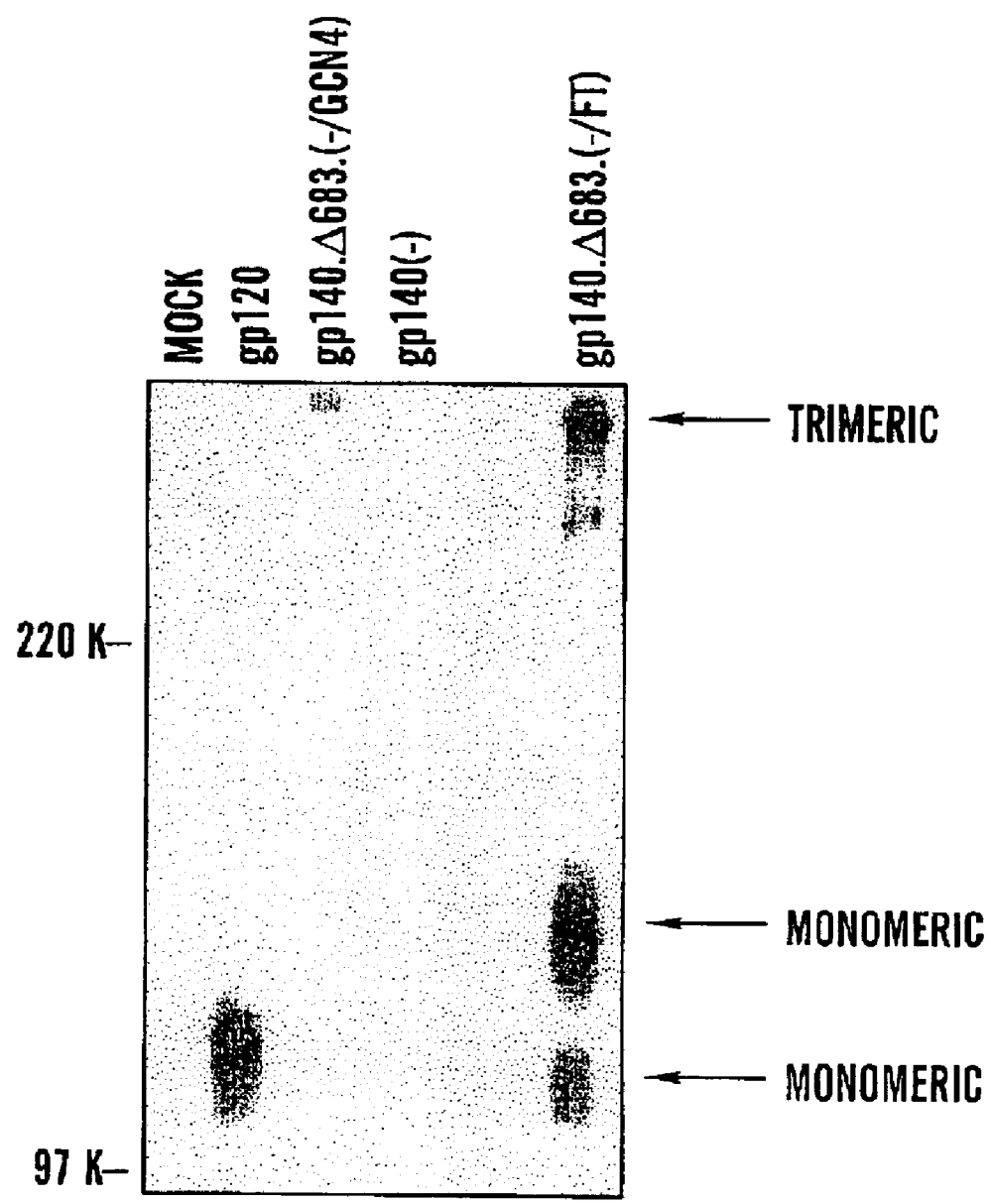

The glycoproteins shown in FIG. 9 were transiently expressed in 293T cells and labeled with $^{35}$S-methionine/ cysteine. The $^{35}$S-labeled proteins were then immunoprecipitated with pooled sera of HIV-1-infected patients and resolved on a 7.5% SDS-PAGE gel. As previously shown, gp120 and gp140(-) were observed as monomeric on this type of gel and the gp140 683(-/GCN4) glycoprotein contained two forms, a reduced form of 140 kD and a high order form of about 400 kD which is consistent with a trimeric form (FIG. 10). Shown in the right lane of FIG. 10 is the gp140 683(-/FT) glycoprotein which contained a similar high order form of around 400 kD and two reduced forms of 140 kD and 120 kD likely representing the un-cleaved and cleaved glycoproteins respectively.

Figures 11A, 11B, 11C:
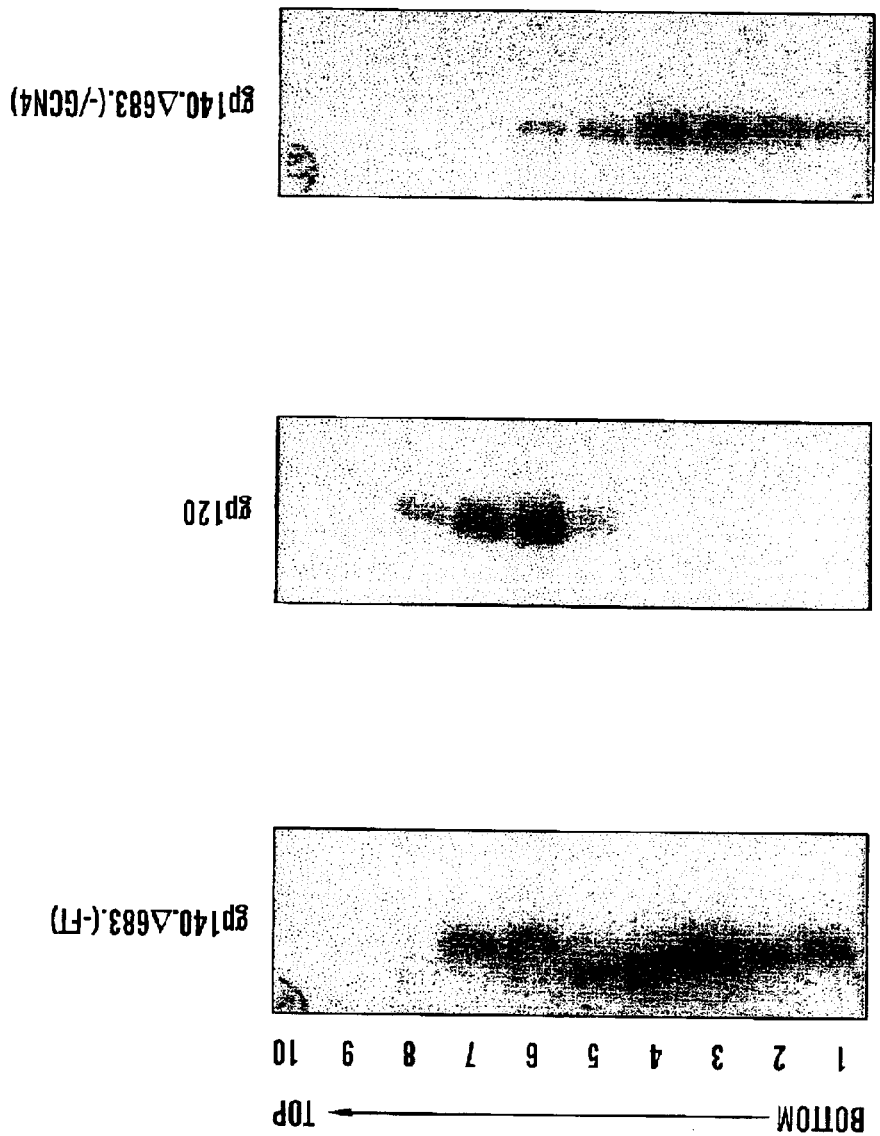

$^{35}$S-labeled proteins were concentrated about 4-fold using Centriprep YM-30 filters (Amicon) and analyzed on 10.3 columns of 10% to 25% sucrose gradient (FIGS. 11A–C). 1.1 ml fractions were taken manually, and protein distributions were analyzed by immunoprecipitating the proteins in each fraction with pooled sera of HIV-1-infected patients. Monomeric gp120 located in the fractions 6–7 as shown in FIG. 11B, while trimeric gp140 of gp140Δ683(-/GCN4) mainly concentrated in fractions 34 in FIG. 11C panel. The column bottom (fraction 1) probably contained some high order aggregates of the glycoprotein. In FIG. 11A, the majority of gp140Δ683(-/FT) glycoprotein was in the fraction 3–4, which is consistent with a trimeric form, and the cleaved portion, as seen on the SDS-PAGE of FIG. 10, was in fractions 6–7, which is consistent with a monomeric form (Note: the column was shifted half of a fraction to the bottom due to a over-taking of fraction 1 up to about 1.7 ml).

Figure 12A:
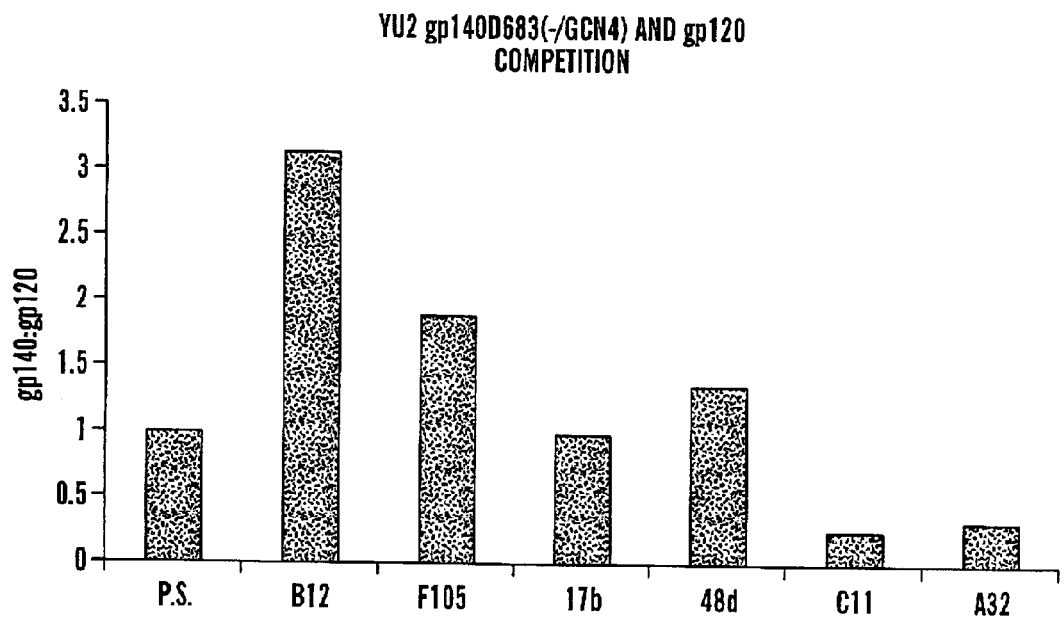
Figure 12B:
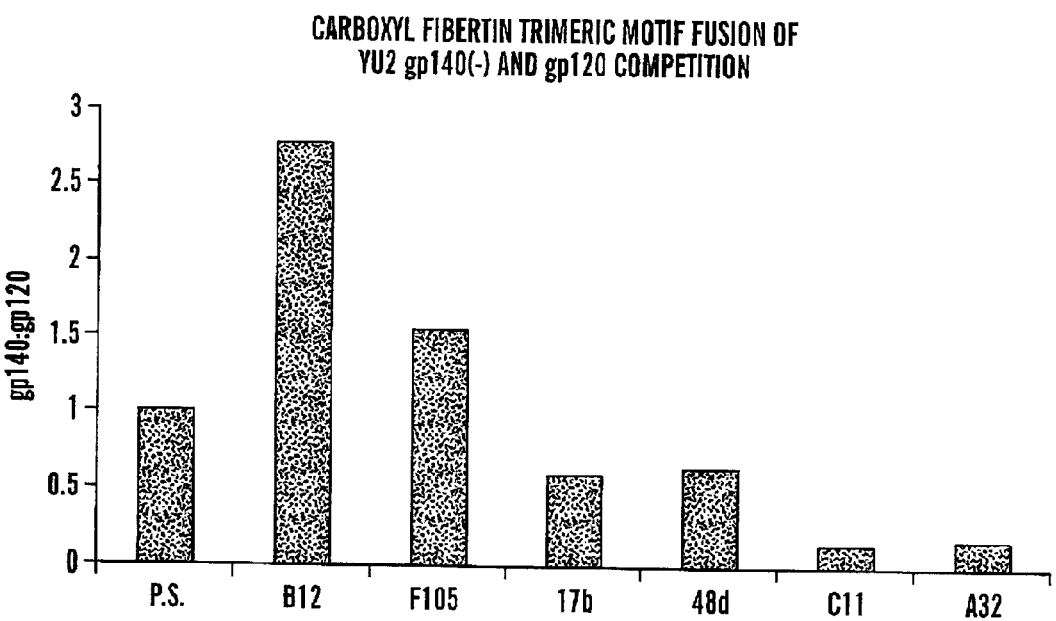

$^{35}$S-labeled gp120 was mixed with a similar amount of $^{35}$S-labeled gp140 683(-/FT) or gp140 683(-/FT) proteins (FIGS. 12A and). FIG. 12A shows the results when GCN4 is used and FIG. 12B shows the results when the Fibritin trimeric motif is used. The proteins were then allowed to compete to bind a panel of monoclonal antibodies in these mixtures. 3 l of pooled patient sera or 1 g of purified monoclonal antibodies were used in each competition assay in a standard immunoprecipitation format. The bound proteins were then resolved on a 7.5% SDS-PAGE gel (20×16 cm) and quantified by a Phosphor-Imager screen. The ratio of gp140 to gp120 for each antibody were calculated and normalized to that of the pooled patient sera. The bigger the gp140:gp120 ratio is, the higher the relative affinity of the gp140 trimer is to this specific monoclonal antibody. The profile of the gp140:gp120 ratio of a gp140 glycoprotein is reflective of the exposure or accessibility of the immunoepitopes on the trimeric complex. In this panel of monoclonal antibodies, B12 is highly neutralizing, F105 is modestly neutralizing, 17b and 48d are minimally neutralizing, and C11 and A32 are non-neutralizing.

All references described herein are incorporated hereby by reference.

We claim:

1. A stable trimer of three HIV-1 or HIV-2 soluble envelope glycoprotein monomers, wherein each monomer contains a HIV-1 gp120 protein or HIV-2 gp125 protein, referred to as the gp120 protein, wherein at least one monomer is modified, wherein the modified monomer maintains the overall three-dimensional structure of the wildtype gp120 monomer, wherein a portion of one variable region of the modified monomer has been deleted and wherein a trimeric motif has been added carboxyl to the gp120 protein.

2. The stable trimer of claim 1, wherein the modified monomer further comprises a linker inserted at a site corresponding to the natural cleavage site between the gp120 protein and the transmembrane protein (gp41), wherein the natural cleavage site has been disrupted.

3. The trimer of claim 1, wherein each modified monomer does not contain amino acid residues corresponding to its transmembrane region and its gp120/gp41 cleavage site.

4. The trimer of claim 3, wherein each modified monomer does not contain the transmembrane and cytoplasmic regions of gp41.

5. The trimer of claim 4, wherein a disulphide bridge is introduced within the coiled coil structure.

6. The trimer of claim 3 or 4, wherein the HIV-1 monomer is modified such that the monomer terminates at a site corresponding to amino acid residue Leu 593 of HIV-1 strain YU2, and wherein a cysteine pair and a glycine residue at the carboxy terminus end of the precursor have been added or substituted for other amino acid residues.

7. The trimer of claim 1, wherein the monomer is modified such that the monomer terminates immediately N-terminal to the transmembrane region, and the natural cleavage site between gp120/gp41 of the precursor of the HIV-1 gp120 protein is not present.

8. The trimer of claim 7, wherein a disulphide bridge is introduced within a coiled coil structure corresponding to the coiled coil structure of a HIV-1 gp41 protein.

9. The trimer of claim 7 or 8, wherein a cysteine pair and a glycine residue at the carboxy terminal end of the precursor of the HIV-1 gp122 have been added or substituted for other amino acid residues.

10. The trimer of claim 1, wherein the trimeric motif is the carboxy terminus of each monomer.

11. The trimer of claim 3 or 4, wherein the trimeric motif is the carboxy terminus of each monomer.

12. The trimer of claim 7 or 8, wherein the trimeric motif is the carboxy terminus of each monomer.

13. The trimer of claim 1, wherein a trimeric motif is inserted N-terminal to a site corresponding to a transmembrane region in a precursor to the gp120 protein, and wherein said transmembrane region is deleted or substituted, and a site in the precursor to the gp120 protein corresponding to a natural cleavage site between its transmembrane protein and the gp120 protein has been disrupted.

14. The trimer of claim 13, wherein the trimeric motif is a coiled coil.

15. The trimer of claim 14, wherein the protein terminates after the coiled coil.

16. The trimer of claim 1, wherein the trimeric motif is a GCN4 trimeric motif or a fibritin trimeric motif.

17. The trimer of claim 1, wherein the trimeric motif is SEQ ID NO:1.

18. The protein of claim 1, wherein the trimeric motif is SEQ ID NO:4.

* * * * *